(12) United States Patent
Flint et al.

(10) Patent No.: US 6,642,036 B2
(45) Date of Patent: Nov. 4, 2003

(54) SINAPOYLGLUCOSE:MALATE SINAPOYLTRANSFERASE FORM MALATE CONJUGATES FROM BENOZIC ACID GLUCOSIDES

(75) Inventors: Dennis Flint, Newark, DE (US); Knut Meyer, Wilmington, DE (US); Paul Viitanen, West Chester, PA (US)

(73) Assignee: E. I. Du Pont de Nemours and Company, Wilmington (DE)

( * ) Notice: Subject to any disclaimer, the term of this patent is extended or adjusted under 35 U.S.C. 154(b) by 0 days.

(21) Appl. No.: 09/896,866

(22) Filed: Jun. 29, 2001

(65) Prior Publication Data
US 2002/0151002 A1 Oct. 17, 2002

Related U.S. Application Data

(60) Provisional application No. 60/216,615, filed on Jul. 7, 2000.

(51) Int. Cl.$^7$ .................................................. C12P 7/62
(52) U.S. Cl. .................. 435/135; 435/41; 435/193; 435/252.33; 435/320.1; 536/23.2
(58) Field of Search ...................... 435/41, 135, 193, 435/252.33, 320.1; 536/23.2

(56) References Cited

FOREIGN PATENT DOCUMENTS

| DE | 4423022 C1 | 5/1995 |
|----|------------|--------|
| WO | WO 9600788 | 1/1996 |
| WO | WO 0018943 A1 | 4/2000 |

OTHER PUBLICATIONS

Mock et al., "Sinapoylglucose: Malate sinapoyltransferase actifity in *Arabidopsis thaliana* and *Brassica rapa*", Zeitschrift Fuer Naturforschung, Section C. Biosciences, vol. 9/10, No. 47, 1992, pp. 680–682, XP008003616.

Lorenzen et al., Sinapic Acid Ester Metabolism in Wild Type and a Sinapoylglucose–Accumulating Mutant of Arabidopsis, Plant Physiology, vol. 112, No. 4, Dec. 1996, pp. 1625–1630, XP002199993.

Datebase EMBL Online, EBI, Jul. 2000, Lehfeldt et al., *Arabidopsis thaliana* sinapoylglucose: malate sinapoyltransferase (SNG1) mRNA, complete cds, Database accession No. AF 275313, CP002200002.

Lehfeld et al., Cloning of the SNG1 gene of Arabidopsis reveals a role for a serine carboxypeptidase–like protein as an acyltransferase in secondary metabolism, The Plant Cell, vol. 12, No. 8, Aug. 2000, pp. 1295–1306, XP002199994.

Database EMBL Online, EBI; Aug. 1, 1998, Lehfeldt et al., Sinapoylglucose: malate sinapoyltransferase, XP002200003.

Li et al., "An acyltransferase catalyzing the formation of diacylglucose is a serine carboxypeptidase–like protein", Proceedings of the National Academy of Sciences of the United States, vol. 97, No. 12, Jun. 6, 2000, pp. 6902–6907, XP002199998.

Seibert et al., FEBS Lett vol. 307: pp. 347–350, 1992.

Nichols et al., J. Bacteriol. vol. 174: pp. 5309–5316, 1992.

Loscher and Heide, Plant Physiol. vol. 106: pp. 271–279, 1994.

Severin et al., Planta Medica, vol. 59, No. 7, pp. A590–A591, 1993.

Siebert et al., Plant Physiol. vol. 112: pp. 811–819, 1996.

Mock and Strack, Phytochemistry, vol. 32: pp. 575–579, 1993.

Strack, Planta, vol. 155: pp. 31–36, 1982.

Strack, Planta, vol. 163: pp. 563–568, 1985.

Strack et al., Z. Naturforsch 38c: pp 21–27, 1983.

Graewe et al., Planta 187 (2): 236–241, 1992.

Lin et al., Accession No. AC004401, *Arabidopsis thaliana*.

Wu et al., Accession No. M96268, *Escherichia coli*.

Lin et al., Accession No. AAC17816, *Arabidopsis thaliana*.

*Primary Examiner*—Ponnathapu Achutamurthy
*Assistant Examiner*—Christian L Fronda

(57) ABSTRACT

A gene has been isolated from Arabidopsis encoding sinapoylglucose:malate sinapoyltransferase (SMT). SMT is responsible for the substitution of a glucose moiety on aromatic acid glucosides with a malate moiety in plant vacuoles. The enzyme is useful for the production of small molecules for materials manufacture.

4 Claims, 9 Drawing Sheets

SINAPOYLGLUCOSE:MALATE SINAPOYLTRANSFERASE FORM MALATE CONJUGATES FROM BENOZIC ACID GLUCOSIDES

This application claims the benefit of U.S. Provisional Application No. 60/216,615, filed Jul. 7, 2000.

FIELD OF THE INVENTION

This invention is in the field of plant molecular biology. More specifically, this invention pertains to nucleic acid fragments encoding plant sinapoylglucose:malate sinapoyltransferase (SMT) and its use in the conjugation of small molecules for materials.

BACKGROUND OF THE INVENTION

Recent advances in genetic engineering have enabled the development of new biological platforms for the production of molecules, heretofore only synthesized by chemical routes. Although advances in fermentation technology have resulted in the use of microorganisms for the production of pharmaceutically useful proteins (antibiotics, enzymes etc.), the possibility of using green plants for the manufacture of high volume materials is becoming increasingly more attractive.

There are two obvious advantages of using green plants to produce large amounts of compounds that are traditionally synthetically manufactured. First, plants are a renewable energy resource. The photosynthetic ability of green plants means that the only raw materials that are required to produce carbon-based compounds in plants are $CO_2$, water and soil nutrients. Second, in contrast to microbial fermentation, green plants represent a huge biomass that can easily accommodate the large amounts of chemicals that are required for high-volume, low-cost applications. The use of plants as production platforms for materials is complicated only in that they comprise a vastly more differentiated and complex genetic and biochemical systems as compared with microbes. Thus, production of molecules and materials from plants will be greatly enhanced if the materials to be produced are native, at least in some amounts to the plant.

Two classes of materials that are native to plants are aromatic acids and aromatic esters. In particular, p-hydroxybenzoic acid (pHBA) and esters of pHBA can readily be found. Both of these materials find use in various polymers useful in paints and other coatings. In addition, pHBA is the key monomer in Liquid Crystal Polymers (LCPs) which contain approximately 67% pHBA. Esters of pHBA can be used as backbone modifiers in other condensation polymers, i.e., polyesters, and are also used to make parabens preservatives.

It is known that aromatic acids, aromatic esters and pHBA are endogenous to plants as well as other organisms. In most bacteria, the generation of pHBA occurs by way of chorismate, an important branchpoint intermediate in the synthesis of numerous aromatic compounds, including phenylalanine, tyrosine, p-aminobenzoic acid and ubiquinone. In *E. coli*, chorismate itself undergoes five different enzymatic reactions to yield five different products, and the enzyme that is ultimately responsible for the synthesis of pHBA is chorismate pyruvate lyase, which is also known as CPL. The latter is the product of the *E. coli* ubiC gene, which was independently cloned by two different groups (Siebert et al., *FEBS Lett* 307:347–350 (1992); Nichlols et al., *J. Bacteriol* 174:5309–5316 (1992)). In higher plants the biosynthetic pathway leading to pHBA in *Lithospermum erythrorhizon* is thought to consist of up to ten successive reactions (Lsscher and Heide, *Plant Physiol.* 106:271–279 (1992)), presumably all catalyzed by different enzymes.

Recently it has been shown that levels of pHBA production in plants may be enhanced through genetic manipulation. Several recent publications (Severin et al., *Planta Medica*, (1993) Vol. 59, No. 7, pp. A590–A591; Siebert et al., *Plant Physiol.* 112:811–819 (1996); WO 9600788), including Applicants own work (U.S. Ser. No. 09855,341) have demonstrated that tobacco plants (*Nicotiana tabacum*) transformed with a constitutively expressed chloroplast-targeted version of *E. coli* CPL (referred to as "TP-UbiC") have elevated levels of pHBA that are at least three orders of magnitude greater than wildtype plants. However, it should be noted that these studies indicated that virtually all of the pHBA was converted to its two glucose conjugates, a phenolic glucoside and an ester glucoside. The conversion of the glucoside to a useful product will require a chemical step and represents an obstacle for the production of free pHBA or other aromatic acids. Therefore, a method of further processing the pHBA glucosides is needed.

There are no reports of endogenous plant transconjugation reactions that involve the transfer of benzoic acids from glucose esters to organic acids. However, there are reports of the processing of esters of hydroxycinnamic acids such as sinapic acid to malate conjugates as a function of secondary metabolism in cotyledon and leaf tissues of cruciferous plant species. Sinapic acid is generated from phenylalanine through the action of phenylalanine ammonia lyase (PAL) cinammate-4-hydroxylase, coumarate-3-hydroxylase, caffeic acid o-methyltransferase and ferulate-5-hydroxylase. Sinapoyl glucose is synthesized from sinapic acid and uridinediphosphate glucose (UDPG) through the action of UDPG sinapoyltransferase (SGT). Sinapoyl glucose is subsequently translocated to the vacuole. Sinapoyl glucose is a 1-O-glucose ester that has a free energy of hydrolysis (Mock and Strack, *Phytochemistry* 32:575–579 (1993)). This linkage provides the necessary free energy for the transacylation reaction catalyzed by sinapoylglucose:malate sinapoyltransferase (SMT) (Strack, *Planta* 155:31–36 (1982)), which generates sinapoyl malate in the expanding cotyledons (Sharma and Strack, *Planta* 163:563–568 (1985)). It is instructive to note that sinapoyl malate accumulated in the vacuole in these plants, although little is known about how vacuolar transport might be effected (Sharma and Strack (1985), supra). During seed maturation, sinapic acid is converted to sinapoyl choline by the combined actions of SGT and sinapoylglucose:choline sinapoyltransferase (SCT) (Strack et al., *Z Naturforsch* 38c:21–27 (1983)). Recently SMT has been partially characterized (Graewe et al., *Planta* 187(2):236–41 (1992)). However, despite the detailed biochemical understanding of these enzymes, none of the genes involved had been cloned, and relatively little is known about their regulation. Additionally, it is unclear how or if this enzymatic system may be adapted to the processing of benzoic acid glucosides and related molecules.

The problem to be solved therefore is to design a system for the production of benzoic acid derivatives and particularly pHBA derivatives in plants. Applicants have solved the stated problem by the discovery that sinapoylglucose:malate sinapoyltransferase (SMT) has the ability to convert glucosides of p-hydroxybenzoic acid to its corresponding malate conjugate where the malate product is localized in the plant vacuole. This further processing of the native p-hydroxybenzoic acid glucoside advances the art of materials production from genetically modified green plant platforms.

SUMMARY OF THE INVENTION

The present invention provides a method for the production of malate conjugated aromatic acids comprising: contacting a glycosylated aromatic acid with an effective amount of sinapoylglucose:malate sinapoyltransferase which catalyzes the substitution of a glucose moiety on the glycosylated aromatic acid with a malate moiety to form a malate conjugated aromatic acid. Suitable aromatic acids are described by the formula

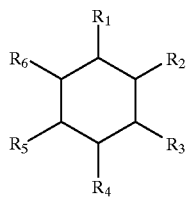

wherein
$R_1$–$R_6$ are each independently H, or OH, or COOH or $OR_7$ or $R_7COOH$ and $R_7$ is $C_1$ to $C_{20}$ substituted or unsubstituted alkyl or substituted or unsubstituted alkenyl or substituted or unsubstituted alkylidene;
providing at least one of $R_1$–$R_6$ is COOH In an alternate embodiment the invention provides a method for the production of carboxylic acid conjugated aromatic acids comprising: contacting a glycosylated aromatic acid with an α-hydroxycarboxylic acid of the general formula:
R—COOH, where R is $C_1$ to $C_{20}$ substituted or unsubstituted alkyl or substituted or unsubstituted alkenyl or substituted or unsubstituted alkylidene;
and an effective amount of sinapoylglucose:malate sinapoyltransferase which catalyzes the substitution of a glucose moiety on the glycosylated aromatic acid with the α-hydroxycarboxylic acid to form a carboxylic acid conjugated conjugated aromatic acid.

In another embodiment the invention provides a method for the production of aromatic esters comprising:
contacting a glycosylated aromatic acid with an alcohol of the general formula:
R—OH, where R is $C_1$ to $C_{20}$ substituted or unsubstituted alkyl or substituted or unsubstituted alkenyl or substituted or unsubstituted alkylidene;
and an effective amount of sinapoylglucose:malate sinapoyltransferase to form an aromatic ester.

Preferred aromatic acids of the invention include para-hydroxybenzoic acid. Preferred α-hydroxycarboxylic acids of the invention include lactate. Preferred alcohols of the invention include methanol, ethanol and isopropanol.

In a preferred embodiment the invention provides a method for the production of pHBA malate comprising a) providing a host cell producing suitable levels of glycosylated pHBA; b) introducing into the host cell a nucleic acid molecule encoding sinapoylglucose:malate sinapoyltransferase; wherein the sinapoylglucose:malate sinapoyltransferase catalyzes the substitution of a glucose moiety on the glycosylated pHBA with a malate moiety to form pHBA malate.

BRIEF DESCRIPTION OF THE DRAWINGS AND SEQUENCE DESCRIPTIONS

Figure 1:
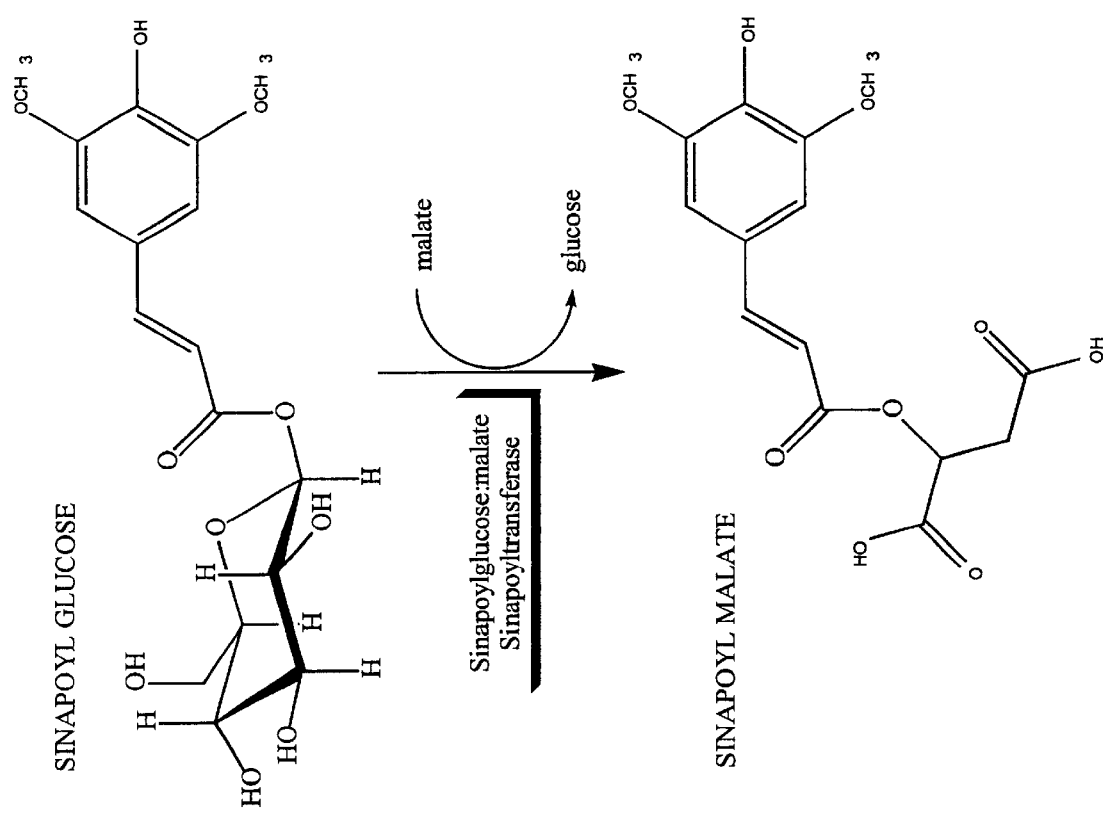
FIG. 1 illustrates the conversion of sinapoyl glucose to sinapoyl malate via sinapoylglucose:malate sinapoyltransferase.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the amino acid sequence of the SMT protein (Genbank accession number AAC17816) produced by conceptual translation of the nucleotide sequence of the SMT gene (Genbank accession number: AC004401).

SEQ ID NO:2 is the nucleotide sequence of the oligonucleotide primer used to amplify a variant of the SMT gene encoding SMT protein devoid of first 19 amino acids of putative signal peptide.

SEQ ID NO:3 is the nucleotide sequence of the restriction site PagI.

SEQ ID NO:4 is the nucleotide sequence of the oligonucleotide primer used to amplify variant of SMT gene.

SEQ ID NO:5 is the nucleotide sequence of the coding region of the SMT transcript (Genbank accession number AC004401).

SEQ ID NO:6 is the nucleotide sequence of the SMT gene variant that is amplified from a DNA template of SEQ ID NO:5 using oligonucleotides of SEQ ID NO:2 and SEQ ID NO:4.

SEQ ID NO:7 is the predicted amino acid sequence of the SMT protein encoded by the SMT gene variant of SEQ ID NO:6.

SEQ ID NO:8 is the nucleotide sequence of the oligonucleotide primer used for amplification of a SMT gene variant that is suitable for expression of SMT in plants.

SEQ ID NO:9 is the nucleotide sequence of the SMT gene variant that is amplified from a DNA template of SEQ ID NO:5 using oligonucleotides of SEQ ID NO:8 and SEQ ID NO:4.

SEQ ID NO:10 is the 5' primer useful for introducing *E. coli* CPL, having Genbank accession No. M96268, into the *E. coli* expression vector, pET-24a (+) (Novagen).

SEQ ID NO:11 is the 3' primer useful for introducing *E. coli* CPL, having Genbank accession No. M96268, into the *E. coli* expression vector, pET-24a (+) (Novagen).

SEQ ID NO:12 is the nucleotide sequence of the ORF of *E. coli* CPL, having Genbank accession No. M96268, in the *E. coli* expression vector, pET-24a (+) Novagen).

SEQ ID NO:13 is the primary amino acid sequence of the ORF of *E. coli* CPL, having Genbank accession No. M96268, in the *E. coli* expression vector, pET-24a (+) (Novagen).

SEQ ID NO:14 is the 5' primer useful for the amplification of the chloroplast targeting sequence of the tomato Rubisco small subunit precursor, for expression of TP-CPL in *E. coli*.

SEQ ID NO:15 is the 3' primer useful for the amplification of the chloroplast targeting sequence of the tomato Rubisco small subunit precursor, for expression of TP-CPL in *E. coli*.

SEQ ID NO:16 is the nucleotide sequence of the ORF of the chloroplast-targeted CPL fusion protein (TP-CPL) in the *E. coli* expression vector, pET-24a (+) Novagen).

SEQ ID NO:17 is the primary amino acid sequence of the ORF of the chloroplast-targeted CPL fusion protein (TP-CPL) in the *E. coli* expression vector, pET-24a (+) (Novagen).

SEQ ID NO:18 is the 5' primer useful for the amplification of the predicted chloroplast cleavage product of TP-CPL (TP-CPL), and its insertion into the *E. coli* expression vector, pET-24d (+) (Novagen).

SEQ ID NO:19 is the 3' primer useful for the amplification of the predicted chloroplast cleavage product of TP-CPL (TP-CPL), and its insertion into the *E. coli* expression vector, pET-24d (+) (Novagen).

DETAILED DESCRIPTION OF THE INVENTION

The present invention provides a gene encoding a sinapoylglucose:malate sinapoyltransferase (SMT) enzyme located in the vacuole of the plant cell which has the ability to conjugate various glycosylated aromatic acids with malate. The gene has been used for the recombinant expression of the SMT protein and its activity has been confirmed by in vitro assays. In addition to its natural substrates, SMT has shown an affinity for p-hydroxybenzoic acid glucosides.

The SMT gene encodes a key enzyme in secondary metabolism of soluble hydroxycinnamic acid esters, converting sinapoyl glucose to sinapoyl malate (FIG. 1). The unexpected affinity of sinapoylglucose:malate sinapoyltransferase for benzoic acid glucosides suggests that this enzyme may be used to facilitate the production of malate conjugated momomeric species in the vacuolar compartment of plant cells, which may later be isolated and used in the synthesis of various polymers.

Figure 2:
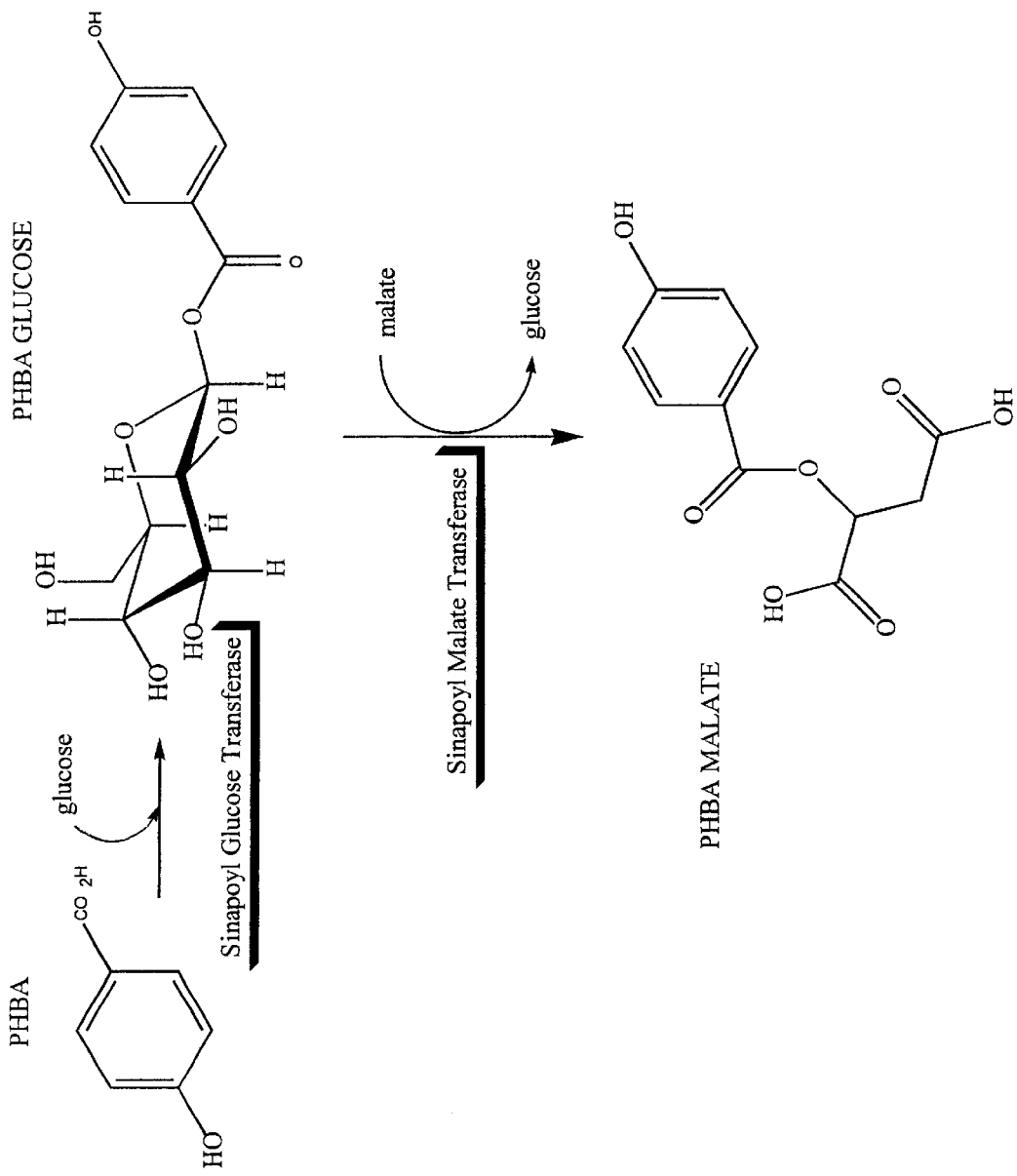
FIG. 2 illustrates the conversion of pHBA glucose to pHBA malate via sinapoylglucose:malate sinapoyltransferase.

The present method may be used for the production of several useful products. For example, an aromatic acid glucoside, such as pHBA glucoside, will be converted to the corresponding malate conjugate (FIG. 2). The end product may be hydrolyzed to release the acid in free form as well as the malate moiety. Malate is useful in a number of chemical processes and is far more valuable than the glucose starting material. Similarly, the conjugated aromatic acid may be used intact as a polymer additive.

In this disclosure, a number of terms and abbreviations are used. The following definitions are provided.

"Open reading frame" is abbreviated ORF.

"Polymerase chain reaction" is abbreviated PCR.

"CPL" is the abbreviation for chorismate pyruvate-lyase.

"SMT" refers to the enzyme sinapoylglucose:malate sinapoyltransferase.

"SNG1" refers to "sinapoylglucose accumulator 1" and represents the gene encoding sinapoylglucose:malate sinapoyltransferase.

"SNG1" refers to the sinapoylglucose accumulator 1 gene locus.

"SGT" is the abbreviation for UDPG sinapoyltransferase, responsible for the conversion of sinapic acid to sinapoly glucose.

"pHBA" is the abbreviation for p-hydroxybenzoic acid.

"sg" is the abbreviation for sinapoyl glucose.

"sm" is the abbreviation for sinapoyl malate.

"HPLC" is the abbreviation for high pressure liquid chromatography.

The term "alkyl" will mean a univalent group derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively.

The term "alkenyl" will mean an acyclic branched or unbranched hydrocarbon having one carbon—carbon double bond and the general formula $C_nH_{2n}$. Acyclic branched or unbranched hydrocarbons having more than one double bond are alkadienes, alkatrienes, etc.

The term "alkylidene" will mean the divalent groups formed from alkanes by removal of two hydrogen atoms from the same carbon atom, the free valencies of which are part of a double bond (e.g. $(CH_3)_2C$=propan-2-ylidene).

As used herein the term "aromatic acid" refers to an acid comprising an aromatic ring that is a suitable substrate for the SMT enzyme, when glycosylated. The natural aromatic acid glucoside substrate for SMT is sinapoyl glucose, for example.

As used herein, an "isolated nucleic acid molecule" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Typically hybridizations will be washed with 2×SSC, 0.1% SDS followed by 0.1×SSC, 0.1% SDS to visualize the results. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant SMT polypeptides as set forth in SEQ ID NO:7. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065;WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals such as transit peptides.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein. Furthermore, a "signal peptide" is an amino acid sequence which is translated in conjunction with a protein and directs the protein to the secretory system (Chrispeels et al., *Ann. Rev. Plant Phys. Plant Mol. Biol.* 42:21–53 (1991)). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel et al., *Plant Phys.* 100:1627–1632 (1992)).

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

Sinapoylglucose:malate Sinapoyltransferase Substrates and Products:

The instant invention provides a gene (SNG1) encoding sinapoylglucose:malate sinapoyltransferase (SMT) which converts various aromatic acid glucosides to the corresponding malate conjugate in the presence of malate. In nature the SNG1 gene converts sinapoyl glucose (the glucoside of sinapic acid) to the malate derivitized form, sinapoyl malate. Unexpectedly, it has been found that SMT will also catalyze the malate conjugation of other aromatic acid glucosides, unrelated to sinapic acid. For example, pHBA glucose (the glucoside of pHBA) has been shown to be converted to pHBA malate in the presence of SMT. Accordingly, suitable substrates for SMT are those of the formula

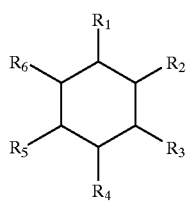

wherein $R_1$–$R_6$ are each independently H, or OH, or COOH or $OR_7$ or $R_7COOH$; and $R_7$ is $C_1$ to $C_{20}$ substituted or unsubstituted alkyl or substituted or unsubstituted alkenyl or substituted or unsubstituted alkylidene; providing at least one of $R_1$–$R_6$ is COOH. Preferred substrates will include benzoic acid glucosides such as pHBA glucose.

SMT may be derived from a variety of plant species and particularly the cruciferous vegetables. Suitable sources of SMT will include but are not limited to broccoli, cauliflower, cabbage, parsnips, radish, kale, turnip, mustard, oil seed rape and members of the Brassica genus generally.

Although SMT demonstrates the ability to replace the glucose moiety of a glycosylated aromatic acid with malate, it will be appreciated that other straight chain carboxylic acids may be substituted for malate. For example, Applicants have discovered that SMT also has the ability to substitute lactate for glucose under the appropriate conditions. Thus, it is contemplated that malate may be substituted with α-hydroxycarboxylic acids which include those of the general formula: R—COOH, where R is $C_1$ to $C_{20}$ substituted or unsubstituted alkyl or substituted or unsubstituted alkenyl or substituted or unsubstituted alkylidene.

Similarly, it has been discovered that malate may also be replaced by alcohols. So for example, Applicants have found that glycosylated pHBA reacted in the presence of methanol, ethanol or isopropanol and SMT will give the corresponding methyl, ethyl or isopropyl ester. Consequently, it is expected that malate by be substituted for alcohols of the general formula: R—OH, where R is $C_1$ to $C_{20}$ substituted or unsubstituted alkyl or substituted or unsubstituted alkenyl or substituted or unsubstituted alkylidene.

Recombinant Microbial Expression:

It will be useful to recombinantly express the SNG1 gene in a microbial platform. The recombinant production of the enzyme will be useful for the production of protein in the generation of antibodies, or large amounts of enzyme for in vitro catalysis. In a preferred embodiment, microbial hosts will be used for the synthesis of malate conjugates of aromatic acids in fermentation processes.

Preferred heterologous host cells for expression of the instant genes and nucleic acid molecules are microbial hosts. Specific suitable hosts include but are not limited Aspergillus, Trichoderma, Saccharomyces, Pichia, Candida, Hansenula, Salmonella, Bacillus, Acinetobacter, Rhodococcus, Streptomyces, Escherichia and Pseudomonas, where *E. coli* is most preferred.

In nature the SMT enzyme is comprised of a mature polypeptide, comprising an additional nineteen amino acids at the N-terminal region which function as a vacuolar targeting sequence. This native sequence is given in SEQ ID NO: 1. The targeting sequence is needed for effective targeting and expression in plants, where it is normally cleaved at the vacuole. However, in recombinant bacteria, and other organisms lacking the plant processing mechanisms, the targeting sequence interferes with expression. Thus, for effective bacterial expression the N-terminal region of the protein is modified to remove the first nineteen N-terminal amino acids and replace them with a start codon recognized by the host (e.g. ATG). In this fashion, only the mature protein is expressed (SEQ ID NO:7).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

Expression in Transgenic Plants:

The SNG1 gene may be used to create transgenic plants having the ability to express SMT. Transgenic plants comprising a functioning SNG1 gene will be useful for the conjugation of aromatic acid glucosides to malate derivatives and their accumulation in plant organelles for eventual purification and use in synthetic processes.

Preferred plant hosts will be any variety that will support a high production level of the SMT protein. Suitable green plants will included but are not limited to of soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (Triticum sp), barley (*Hordeum vulgare*), oats (*Avena sativa, L*), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees and forage grasses.

In one embodiment it is preferred if the plant expressing SNG1 is also capable of producing an aromatic acid glucoside. In some cases, depending on the plant host, aromatic acid glucosides will be naturally produced. In these situations it may be necessary to genetically modify the natural genetic machinery of the plant host such that the desired acid glucoside is overproduced. In other situations it may be necessary to insert foreign genes into the plant host for the production of the desired glycosylated aromatic acid.

In a preferred embodiment, Applicants have engineered a plant host to produce pHBA glucoside by the insertion of a bacterial chorismate pyruvate lyase gene (CPL) which converts 1 mol of chorismate to 1 mol of pyruvate and 1 mol of pHBA. The most well characterized CPL gene has been isolated from *E. coli* and bears the GenBank accession number M96268. The substrate for the CPL enzyme is chorsimate which is an important branchpoint intermediate in the synthesis of numerous aromatic compounds, including phenylalanine, tyrosine, p-aminobenzoic acid and ubiquinone. Subsequently the pHBA product is naturally glycosylated by the plant host (Siebert et al., Plant Physiol. 112:811–819 (1996); Li et al., *Plant Cell Physiol.* 38(7) :844–850 (1997)) to produce the SMT substrate.

The present invention further provides recombinant expression cassettes comprising the SNG1 coding region. A recombinant expression cassette will typically comprise a polynucleotide of the present invention (SNG1) operably linked to transcriptional initiation regulatory sequences which will direct the transcription of the SNG1 gene in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A plant promoter fragment can be employed which will direct expression of a SNG1 gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter.

Alternatively, the plant promoter can direct expression of the SNG1 gene in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689, 051), glob-i promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of SNG1 gene. These promoters can also be used, for example, in recombinant expression cassettes to drive expression of antisense nucleic acids to reduce, increase, or alter concentration and/or composition of the SMT protein in a desired tissue. Thus, in some embodiments, the nucleic acid construct will comprise a promoter functional in a plant cell, such as in Zea mays or tobacco, operably linked to SNG1. Promoters useful in these embodiments include the endogenous promoters driving expression of SMT.

In some embodiments, isolated nucleic acids which serve as promoter or enhancer elements can be introduced in the appropriate position (generally upstream) of a nonheterologous form of the SMT polynucleotide so as to up or down regulate its expression. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from SNG1 so as to control the expression of the gene. Expression of SNG1 can be modulated under conditions suitable for plant growth so as to alter the total concentration and/or alter the composition of SMT in a plant cell. Thus, the present invention provides compositions, and methods for making, heterologous promoters and/or enhancers operably linked to a native, endogenous (i.e., nonheterologous) form of SMT.

Where SMT polypeptide expression is desired, it is generally desirable to include a polyadenylation region at the 3'-end of a polynucleotide coding region of SNG1. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1:1183–1200 (1987). Such intron enhancement of gene expression is typically greatest when placed near the 5' end of the transcription unit. Use of maize introns Adh1-S intron 1, 2, and 6, the Bronze-I intron are known in the art. See generally, *The Maize Handbook,* Chapter 116, Freeling and Walbot, Eds., Springer, New York (1994). The vector comprising the SNG1 sequence will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. Enzymol.* 153:253–277 (1987).

Optionally, SNG1 may introduced into a plant. Generally, the gene will first be incorporated into a recombinant expression cassette or vector, by a variety of methods known in the art. See, for example, Weising et al., *Ann. Rev. Genet.* 22:421–477 (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes et al., Direct DNA Transfer into Intact Plant Cells via Microprojectile Bombardment, pp.197–213 in *Plant Cell, Tissue and Organ Culture, Fundamental Methods,* Eds. O. L. Gamborg and G. C. Phillips, Springer-Verlag Berlin Heidelberg, N.Y. (1995). The introduction of DNA constructs using PEG precipitation is described in Paszkowski et al., *Embo J* 3:2717–2722 (1984). Electroporation techniques are described in Fromm et al., Proc. Natl. Acad. Sci. (USA) 82:5824 (1985). Ballistic transformation techniques are described in Klein et al., *Nature* 327:70–73 (1987).

Alternatively, Agrobacterium tumefaciens-mediated transformation techniques may be used. See, for example Horsch et al., *Science* 233:496–498 (1984); Fraley et al., *Proc. Natl. Acad. Sci. (USA)* 80:4803 (1983); and *Plant Molecular Biology: A Laboratory Manual,* Chapter 8, Clark, Ed., Springer-Verlag, Berlin (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (U.S. Pat. No. 5,591,616). Although Agrobacterium is useful primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (e.g., Lichtenstein and Fuller, in *Genetic Engineering,* vol. 6, PWJ Rigby, Ed., London, Academic Press (1987); and Lichtenstein, C. P., and Draper, J. in *DNA Cloning,* Vol. II, D. M. Glover, Ed., Oxford, IRI Press (1985)); Application PCT/US87/02512 (WO 88/02405 published Apr. 7, 1988) describes the use of *A. rhizogenes* strain A4 and its Ri plasmid along with *A. tumefaciens* vectors pARC8 or pARC 16) (2) liposome-mediated DNA uptake (e.g., Freeman et al., *Plant Cell Physiol.* 25:1353 (1984)), (3) the vortexing method (e.g., Kindle, *Proc. Natl. Acad. Sci.,* (USA) 87:1228 (1990)).

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, NY, pp. 124–176 (1983); and *Binding, Regeneration of Plants, Plant Protoplasts,* CRC Press, Boca Raton, pp. 21–73 (1985).

The regeneration of plants from either single plant protoplasts or various explants is well known in the art. See, for example, *Methods for Plant Molecular Biology,* A. Weissbach and H. Weissbach, Eds., Academic Press, Inc., San Diego, Caif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, New York (1994); *Corn and Corn Improvement,* 3$^{rd}$ edition, Sprague and Dudley Eds., American Society of Agronomy, Madison, Wis. (1988). For transformation and regeneration of maize see, Gordon-Kamm et al., *The Plant Cell,* 2:603–618 (1990).

The regeneration of plants containing the SNG1 gene and introduction by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.),* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the SNG1 gene can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Recovery of Free Aromatic Acids from the Conjugate:

pHBA conjugates that are glucose esters or ethers or esters of organic acids can be extracted from plant tissues in water or less polar solvents such as for example methanol or ethanol. Hydrolysis of pHBA esters and ethers can be performed with dilute acid such as hydrochloric acid (0.1 M) or base such as sodium hydroxide (1 M), both at elevated temperatures.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions; Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology, Washington, DC. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Sinapolyglucose:malate Sinapolytransferase (SMT) Enzyme Assay:

Sinapoyl glucose was purified from the sng1 mutant of Arabidopsis as described by Lorenzen et al. (*Plant Physiology* 112:1625–1630 (1996)). The SMT assay contained 12.5 μL of 0.5 mM sinapoyl glucose in 100 mM potassium phosphate buffer (pH 7.5), 5 μL of 100 mM potassium phosphate buffer (pH 6.0), 5 μL of 1 M malic acid in potassium phosphate buffer (pH 6.0) and 5 μL of *E. coli* extract corresponding to 100 μg of protein. Assays were incubated for 14 h at 30° C., stopped by addition of 30 μL of methanol and stored at −70° C. before analysis by HPLC. Enzyme assays were analyzed by HPLC on a Nova-Pak® Pak® C18 column (60 Å pore size, 4 μM particle size) using a gradient from 6% acetonitrile, 1.5% phosphoric acid to 48% acetonitrile, followed by 1.5% phosphoric acid and UV detection at 335 nm.

LC-MS Analysis of PHBA Malate:

HPLC Conditions and Apparatus

An HP 1100 (Hewlett Packard, Calif.) chromatographic system was used to deliver the mobile phase at a flow rate of 0.3 mL/min. The mobile phase consisted of a gradient mixture of two solvents: (A) solvent was 98% water and 2% methanol; (B) solvent was 98% methanol and 2% water. Both solvents contained 10 mM formic acid as a modifier. The column used was an Alltech, Altima C 18 column (2.1×150 mm, 5-μm particle size). The column was equilibrated with 5% B. Following a 10 μL injection of analyte, the gradient used was, 1 min 5% B, 10 min 50% B, 15 min 100% B and 20 min 100% B. UV detection was done at 254 nm. Upon exiting the flow cell the eluent was split 6:1 giving a flow into the mass spectrometer of 50 μL/min.

Condensed Summary—Instrument: HP1100; column: Alltech, Altima C 18, 2.1×150 mm; temperature: 40° C.; injection volume: 10 μL; solvent A: 98% water, 2% acetonitrile+10 μM formic acid; solvent B: 98% acetonitrile, 2% water+10 μM formic acid; flow rate: 0.3 mL/min; UV detection: 254 nm.

Gradient:

| Time (min) | % B |
|---|---|
| 0.0 | 5.0 |
| 1.0 | 5.0 |
| 10.0 | 50.0 |
| 15.0 | 100.0 |
| 20.0 | 100.0 |

Mass Spectrometry

A Micromass Quattro Ultima triple quadrupole mass spectrometer (Micromass, UK) equipped with a Z-spray electrospray interface was used for the detection of analytes. Data was acquired in negative ion mode with a capillary voltage of 3.18 kV and a cone voltage of 81 V. The desolvation gas flow was 337 L/min of nitrogen and the cone gas flow was 41 L/min also of nitrogen. The desolvation temperature was 150° C. and the source block temperature was 110° C. The instrument was tuned for unit resolution. Data was collected in centroid mode by scanning Q1 from 50–500 daltons in 1 sec for MS experiments. For MS/MS experiments Q1 was held at the parent mass with a window width of 1 mass unit while Q3 was scanned from 50–300 daltons in 0.75 sec. Argon was admitted to the collision cell to maintain a collision cell pressure of 2.0e−4 mBar. A collision energy of 20.0 volts was applied to facilitate formation of daughter ions.

Condensed Summary—Instrument: Micromass Quattro Ultima, triple quadrupole ionization mode: electrospray, negative ion; capillary voltage: 3.18 kV; Cone Voltage: 81 V; source block temp: 110 μC; desolvation temp: 150° C.; desolvation gas: nitrogen; desolvation gas flow: 337 L/h; cone gas flow: 41 L/h; mass range: 50–500; tuned for unit resolution.

Construction of CPL Containing Cassettes for the Production of PHBA:

PCR-Cloning of *E. coli* CPL

Two PCR primers were used to amplify the *E. coli* ubiC gene from genomic DNA, while adding unique restriction sites to its flanking regions for subsequent ligation into a high copy number plasmid. This gene codes for chorismate pyruvate lyase, which is referred to below as CPL. The primers used for this purpose were based on the published DNA sequences of the *E. coli* ubic gene (GenBank accession number M96268) and consisted of the following nucleotides:

Primer 1 - (SEQ ID NO: 10):
    5'-CTA CTC ATT Tca tat gTC ACA CCC CGC GTT AA-3'

Primer 2 - (SEQ ID NO: 11):
    5'-CAT CTT ACT aga tct TTA GTA CAA CGG TGA CGC C-3'

The underlined bases hybridize to the target gene, while lower case letters indicate the restriction sites (NdeI or BglII) that were added to the ends of the PCR primers.

Amplification of the *E. coli* ubic gene was achieved using Primers 1 (SEQ ID NO:10) and 2 (SEQ ID NO:11), and genomic DNA from *E. coli* strain W3110 (Campbell et al., *Proc. Natl. Acad Sci.* 75:2276–2284 (1978)). Primer 1 (SEQ ID NO:10) hybridizes at the start of the gene and introduces a NdeI site at the protein's initiation codon, while Primer 2 (SEQ ID NO:11) hybridizes at the opposite end and provides a BglII site just past the termination codon. The 100 μL PCR reactions contained 100 ng of genomic DNA and both primers at a final concentration of 0.5 μM. The other reaction components were provided by the GeneAmp PCR Reagent Kit (Perkin Elmer), according to the manufacturer's protocol. Amplification was carried out in a DNA Thermocycler 480 (Perkin Elmer) for 22 cycles, each comprising 1 min at 94° C., 1 min at 55° C., and 1 min at 72° C. Following the last cycle, there was a 7-min extension period at 72° C.

The PCR product was cut with NdeI and BglII, and the resulting fragment was ligated into the *E. coli* expression vector, pET-24a (+) (Novagen) that had been digested with NdeI and BamHI. The ligation reaction mixture was used to transform *E. coli* DH10B electocompetent cells (GibcoBRL) using a BTX Transfector 100 (Biotechnologies and Experimental Research Inc.) according to the manufacturer's protocol; growth was selected on LB media that contained kanamycin (50 μg/mL). Transformants that contained plasmids with a CPL insert were identified through PCR reactions, using Primers 1 (SEQ ID NO:10) and 2 (SEQ ID NO:11) and individual resuspended colonies as the source of template; from hereon, this technique is simply referred to as "colony PCR". Plasmid DNA was isolated from a representative colony that yielded a PCR product of the correct size, and the entire insert corresponding to the CPL was sequenced completely to check for PCR errors; none were found. The plasmid that was selected for further manipulation is referred to below as "pET24a-CPL". The nucleotide sequence of the ORF for CPL in the pET24a *E. coli* expression construct and its predicted primary amino acid sequence are set forth in SEQ ID NO:12 and SEQ ID NO:13, respectively.

Construction of a Chloroplast-Targeted Version of CPL: TP-CPL

It is known that chorismate is localized in chloroplasts and other types of plastids (Siebert et al., *Plant Physiol.* 112:811–819 (1996)) and it was therefore essential to provide CPL with an N-terminal chloroplast targeting sequence that would efficiently direct the foreign protein to chloroplasts, the site of chorismate production. This was accomplished by constructing a chimeric protein that consists of a chloroplast targeting sequence that is derived from the tomato Rubisco small subunit precursor protein fused to the initiator Met residue of CPL; the resulting fusion protein is referred to below as "TP-CPL". To generate a DNA fragment corresponding to the transit peptide of the Rubisco small subunit and first four amino acid residues of "mature" Rubisco, PCR was employed. The target for amplification was the plasmid pTSS1-91-(#2)-IBI (Siebert et al., *Plant Physiol.* 112:811–819 (1996)), which contains a full-length cDNA clone of the tomato Rubisco small subunit precursor for rbcS2 (Sugita et al., *Mol Gen Genet.* 209:247–256 (1987); Siebert et al., *Plant Physiol.* 112:811–819 (1996)). The following primers were used this reaction:

Primer 3 - (SEQ ID NO: 14):
5'-CTA CTC ACT TAG ATC Tcc atg gCT TCC TCT GTC ATT TCT-3'

Primer 4 - (SEQ ID NO: 15):
5'-CAT CTT ACT cat atg CCA CAC CTG CAT GCA GC-3'

The underlined portion of Primer 3 (SEQ ID NO: 14) hybridizes to the first 21 nucleotides of the Rubisco small subunit precursor and introduces an NcoI site (lower case letters) at the initiator Met residue at the start of the chloroplast targeting sequence. As indicated, this primer also contains a BglII site (bold letters) at its 5' end, that is just upstream from the NcoI site. Primer 4 (SEQ ID NO: 15) hybridizes at the other end of the chloroplast targeting sequence to nucleotides 167–184 of the ORF of the Rubisco small subunit precursor. A unique NdeI site was engineered into this primer (lower case letters) to allow attachment of the PCR fragment containing the chloroplast targeting sequence to the NdeI site that is situated at the start codon of CPL in the pET-24a expression construct. The 100-μL PCR reaction contained ~75 ng of pTS S 1-91-(#2)-IBI and Primers 3 (SEQ ID NO:14) and 4 (SEQ ID NO:15) both at a final concentration of 0.9 M. Amplification was carried out in a DNA Thermocycler 480 (Perkin Elmer) for 25 cycles, each comprising 1 min at 94° C., 1 min at 55° C., and 1 min at 72° C.; the last cycle was followed by a 7-min extension period at 72° C. The PCR product was digested with BglII and NdeI, and ligated into pET24a-CPL that had been cleaved with the same restriction enzymes to remove a small DNA fragment (106 bp) that contained only vector sequence, including the T7 promoter. The ligation reaction mixture was introduced into *E. coli* DH10B using electroporation, and growth was selected on LB media with kanamycin (50 μg/mL). Transformants harboring plasmids with the inserted chloroplast targeting sequence were identified by colony PCR using Primers 2 (SEQ ID NO: 12) and 3 (SEQ ID NO:13). A representative plasmid yielding a PCR product of the correct size was selected for further manipulation; this plasmid is referred to below as "pET24a-TP-CPL". To confirm the absence of PCR errors, the region of the plasmid corresponding to the amplified chloroplast targeting sequence was sequenced completely using custom designed primers. The nucleotide sequence of the ORF for TP-CPL and its predicted primary amino acid sequence are set forth in SEQ ID NO:16 and SEQ ID NO:17, respectively.

Construction of the Expression Plasmid Used for Tobacco and Arabidopsis Transformation To generate a construct that could be used for constitutive expression in tobacco and Arabidopsis, the DNA fragment corresponding to the full-length TP-CPL fusion protein was subcloned into a modified version of plasmid pML63. The latter was derived from pML40, which contains the following genetic elements: a CaMV 35S promoter, a cab leader sequence, the uidA coding region, and the NOS polyadenylation signal sequence. Briefly, the CaMV 35S promoter is a 1.3 kb DNA fragment that extends 8 base pairs past the transcription start site (Odell et al., Nature 303:810–812 (1985)). Operably linked to its 3' end is the cab leader sequence, a 60 bp untranslated double-stranded piece of DNA that was obtained from the chlorophyll a/b binding protein gene 22L (Harpster et al., Mol. Gen. Genet. 212:182–190 (1988)). Fused to the 3' end of the cab leader is the uidA gene (Jefferson et al. (1987) EMBO J 6:3901) that encodes the protein β-glucuronidase (e.g., "GUS"). Finally, attached to 3' end of the GUS gene is an 800 bp DNA fragment containing the polyadenylation signal sequence from the nopaline synthase (e.g. "NOS") gene (Depicker et al., J. Mol. Appl. Genet. 1:561–564 (1982)). These DNA fragments, together comprising a 35S-GUS chimeric gene, were inserted by standard cloning techniques into the vector pGEM9Zf(-) (Promega; Madison Wis.) to yield plasmid pMH40.

Plasmid pML63, which is basically the same as pMH40 but has a truncated version of the 3' NOS terminator sequence, was generated in the following manner. First, pMH40 was digested with Sal I and the two resulting DNA fragments of 4.03 kb and 2.9 kb were re-ligated to yield a plasmid with the 35S promoter/cab22 leader/GUS gene/3' NOS terminator cassette in the opposite orientation. The resulting construct was then digested with Asp718 I and Hind III to release a 770 bp fragment that contained the 3' NOS terminator sequence. The latter was discarded and replaced with a shorter version that was generated by PCR using pMH40 as a template and Primers 9 (SEQ ID NO: 18) and 10 (SEQ ID NO:19).

```
Primer 9 - (SEQ ID NO: 18):
5'-CCC GGG GGT ACC TAA AGA AGG AGT GCG TCG AAG-3'

Primer 10 - (SEQ ID NO: 19):
5'-GAT ATC AAG CTT TCT AGA GTC GAC ATC GAT CTA
GTA ACA TAG ATG A-3'
```

The PCR product was digested with Hind III and Asp718 I to yield a 298 bp fragment that contains 279 bp of the 3' NOS terminator sequence, starting at nucleotide 1277 (the TAA stop codon) and ending at nucleotide 1556 of the published sequence (Depicker et al., J. Mol Appl Genet 1:561–574 (1982)). Ligation of this PCR fragment into pML3 yielded the plasmid pML63.

As indicated above, pML63 contains the GUS coding region under the control of the 35S promoter and a truncated version of the 3' NOS terminator. It therefore contains all of the transcriptional information that is necessary for the constitutive expression of GUS in plants. To generate an analogous construct for TP-CPL, plasmid pML63 was digested with Nco I and EcoRI. This manipulation releases only the GUS gene insert, leaving the regulatory flanking sequences and the rest of the vector intact. Plasmid pet24a-TP-CPL was also treated with NcoI and EcoRI, which liberates the entire coding region of the TP-CPL fusion protein. The small DNA fragment (693 bp) corresponding to the latter was purified by agarose gel electrophoresis and subjected to a standard ligation reaction with the large vector fragment (4.63 bp) that was obtained from cutting pML63 with Nco I and Eco RI. The ligation reaction mixture was introduced into E. coli DH10B using electroporation, and growth was selected on LB media that contained ampicillin (100 μg/mL). Transformants harboring plasmids with the inserted TP-CPL coding sequence were identified by colony PCR using Primers 2 (SEQ ID NO:10) and 3 (SEQ ID NO:11). A representative plasmid that yielded a PCR product of the correct size was selected for further manipulation.

The binary vector that was used for Agrobacterium-mediated, leaf disc transformation of tobacco was the plasmid pZBL1 which was deposited with the ATCC on Jun. 24, 1997 and bears the accession number 209128. pZBL1 contains the origin of replication from pBR322, the bacterial nptI kanamycin resistance gene, the replication and stability regions of the Pseudomonas aeruginosa plasmid pVS1 (Itoh et al, Plasmid (1984), 11(3), 206–20), T-DNA borders described by van den Elzen et al., (Plant Mol. Biol. (1985), 5(3), 149–54) wherein the OCS enhancer (extending from –320 to –116 of the OCS promoter (Greve et al., J. Mol. Appl. Genet. 1:499–511(1983)) that is part of the right border fragment is removed, and a NOS/P-nptII-OCS 3' gene to serve as a kanamycin resistant plant selection marker. For expression of TP-CPL, plasmid pZBL1 was digested with Sal I which cuts at a unique site between the right and left borders that is ideally situated for the insertion of foreign genes and stable integration into the plant genome. To minimize the possibility of re-ligation without an insert, the cut vector was dephosphorylated using Calf Intestinal Alkaline Phosphatase (GibcoBRL) according by the manufacturer's recommendations. To obtain the fragment that would be inserted into the binary vector, plasmid TP-CPL-pML63 was also digested with Sal I. This treatment releases the entire transcriptional unit for the TP-CPL fusion gene (e.g., 35S promoter/cab22 leader/TP-CPL/3' NOS terminator) as a 2.4 kb DNA fragment. The latter was purified by agarose gel electrophoresis and subjected to a standard ligation reaction with the dephosphorylated 11.0 kb fragment that was obtained from pZBL1 as described above. The ligation reaction mixture was introduced into E. coli DH10B using electroporation, and growth was selected on LB media with kanamycin (50 μg/mL). Transformants harboring plasmids with the TP-CPL fusion gene were identified by colony PCR using Primers 2 (SEQ ID NO:11) and 3 (SEQ ID NO:12), and the orientation of the insert was determined by restriction digestion analysis using Kpn I. In the plasmid that was selected for further manipulation, referred to below as "TP-CPL-pZBL1". As described below, this expression construct was used for the transformation of tobacco and Arabidopis for overproduction of PHBA.

Generation of Transgenic Tobacco Plants

Plasmid TP-CPL-pZBL1 was introduced into Agrobacterium tumefaciens strain LBA4404 (Hoekema et al., Nature 303:179–180 (1983)) using the freeze-thaw transformation procedure (Holsters et al, (1978) Mol. Gen. Genet. 163:181–187)). The cells were plated at 28° C. on YEP media (10 g Tryptone, 10 g Yeast Extract, and 5 g NaCl per liter) that also contained kanamycin (1000 μg/mL) and rifampicin (20 μg/mL). Colonies harboring the binary construct were identified by PCR using appropriate primers.

Potted tobacco plants (Nicotiana tabacum cv. Xanthi) for leaf disk infections were grown in a growth chamber maintained for a 14 h, 21° C. day, 10 h, 18° C. night cycle, with approximately 80% relative humidity, under mixed cool white fluorescent and incandescent lights. Agrobacterium-mediated, leaf disk transformations were performed essentially as described by De Blaere et al., (*Meth. Enzymol.* 153:277–292) with the following modifications. Leaf disks, 8 mm in diameter, were prepared from whole leaves using a sterile paper punch and plants that were 4–6 weeks old. Leaf disks were inoculated by submerging them for 30 mins in concentrated solution of Agrobacterium harboring TP-CPL-pZBL1 resuspended to an OD600 of 0.8 in Murashige Minimal Organics media. Inoculated leaf disks were placed directly on media, that contained (per liter) 30 g of sucrose, 1 mg of 6-benzylaminopurine (BAP), 0.1 mg of napthaleneacetic acid, 8 g of agar, and 1 package of Murashige's Minimal Organics Medium that was obtained from GibcoBRL (cat. #23118-029). After incubation for 3 days at 28° C. in the light, leaf disks were transferred to fresh media of the same composition that also contained kanamycin (300 $\mu$g/mL) and cefotaxime (500 $\mu$g/mL) to select for the growth of transformed tobacco cells and eliminate residual Agrobacterium. Leaf disks were incubated under the growth conditions described above for 3 weeks and were then transferred at 3-week intervals to fresh media of the same composition until optimal shoot size was obtained for root induction. Shoots were rooted on media containing (per liter) 1 package of Murashige's Minimal Organics Medium, 8 g of agar, and 10 g of sucrose. Approximately 4 weeks later, the plants were transferred to soil and allowed to grow to maturity in a growth chamber under the conditions described above.

Analysis of Transgenic Tobacco Plants Expressing TP-CPL

As described above, TP-CPL was introduced into tobacco (*Nicotiana tabacum*) using agrobacterium-mediated, leaf disc transformation to determine its influence on the accumulation of PHBA glucosides. The analysis was conducted on leaf tissue that was obtained from 15 tobacco plants (primary transformants) that resulted from different transformation events. The primary transformants exhibited various levels of PHBA glucosides, ranging from 0–2.3% of the total dry weight. This type of variation is typically observed in nearly all plant transformation experiments, and presumably reflects different levels of gene expression that result from so-called "positional" effects (e.g., stable integration of the trait gene at different locations in the genome) and transgene copy number. That a similar phenomena also occurred in the present study is supported by Western blot analysis of the tobacco transformants using antisera directed against purified recombinant *E. coli* CPL. For example, although the majority of the plants (e.g., 14/15) had immunologically detectable levels of the foreign protein, there was considerable variation in the levels of expression. Generally speaking, however, there was a positive correlation between the strength of the Western signal and the accumulation of pHBA glucosides, consistent with previous observations (Siebert et al., *Plant Physiol.* 112:811–819 (1996)); Sommer et al., *Plant Cell Physiol.* 39(11): 1240–1244 (1998); Sommer et al., *Plant Cell Reports* 17:891–896 (1998)).

Based on dry weight, the average PHBA glucoside content of the 5-week-old tobacco plants was 1.12% (+/– 0.186%), where the number in parenthesis is the standard error of the mean. The three best plants in the present study had PHBA glucoside contents that were at least 2% of dry weight.

In longer growth studies, the total PHBA glucoside levels were 0.5%, 1.6%, 7.2%, and 10% of the total dry weight, when samples were analyzed 1, 5, 11, and 13 weeks after transferring the plant to soil. The 13-week value corresponds to a PHBA content of ~4.5% after correcting for the mass of the associated glucose molecule.

Generation and Analysis of Transgenic Arabidopsis Plants Expressing TP-CPL

The artificial fusion protein, TP-CPL, was introduced into Arabidopsis and PHBA glucoside levels were determined. The binary vector carrying the CaMV35S-CPL expression cassette (e.g., TP-CPL-pZBL1) was transformed into Agrobacterium tumefaciens strain C58 C1 Rif (also known as strain GV3101), carrying the disarmed Ti (virulence) plasmid pMP90 (Koncz, C. and Schell, J., *Mol. Gen. Genet.* 204:383–396 (1986)) by electroporation, using available protocols (Meyer et al., *Science* 264:1452–1455 (1994)). The MP90 strain carrying the binary vector with the CPL expression construct was used to transform *Arabidopsis thaliana* plants of the ecotype Columbia with wild type, fah1-2 (Chapple et al., *Plant Cell* 4:1413–1424 (1992)), sng1-1 (Lorenzen et al., *Plant Physiology* 112:1625–1630 (1996)) genetic backgrounds using a published protocol of the vacuum infiltration technique (Clough S. J., Bent A. F., *Plant J.* 16(6):735–43 (1998)). Transgenic seedlings were identified under sterile conditions on standard plant growth media using kanamycin (50 $\mu$g/mL) for selection. Kanamycin resistant seedlings were transferred to soil and cultivated under a 12-hour light/12-hour dark photoperiod at 100 E $m^{-2}s^{-1}$ at 18° C. (dark) and 21° C. (light) in a soil/perlite mixture. Through this procedure, a population of 301 primary transformants derived from independent transformation events was generated. Six weeks after transfer to soil, the transgenic Arabidopsis plants were analyzed for PHBA glucosides using reverse phase HPLC as described below.

Fresh cut leaf material was homogenized in 50% MeOH (5 $\mu$L per mg wet weight), and the resulting extracts were clarified by low-speed centrifugation. An aliquot of the leaf extract was then applied to a Nova-Pak C 18 column (60 angstrom pore size, 4 $\mu$m particle size) using a gradient of acetonitrile (6%–48%) that contained 1.5% phosphoric acid. The pHBA phenolic and ester glucosides were detected by UV absorption at 254 nm, and quantitated using extinction coefficients that were obtained from authentic chemical standards. Of the 272 transgenic Arabidopsis plants that were analyzed, 239 (or ~88%) contained detectable levels of both glucose conjugates, and these were present in about equal amounts. The total pHBA glucoside content of the best overproducer was 10.73% of dry weight, which is very similar to the highest levels that were observed with tobacco using the same construct. The mean value for the entire population of transgenic Arabidopsis plants was 3.35% (+/–0.13%); the number in parenthesis is the standard error of the mean.

Example 1

Recombinant Expression of SNG1 in *E. coli*

Example 1 illustrates the expression of isolated full length genes encoding sinapoylglucose:malate sinapoyltransferase (SMT) in *E. coli*.

The SMT protein (SEQ ID NO: 1) carries a stretch of nineteen amino acids at the N-terminus that is rich in hydrophobic amino acids and very likely represents a signal peptide. Characteristics of this signal peptide are consistent with the features of presequences involved in transport of proteins across endoplasmic reticular membranes as described by von Heijne et al., (*J. Mol. Biol.* 173:243–251 (1984)). The putative site of signal peptide cleavage (VDS-AS) could be predicted using the SignalP package software and a neural network trained on eukaryotic protein sequences available at http://www.cbs.dtu.dk/services/SignalP/described by Nielsen et al. (*Protein Engineering* 10:1–6 (1997)).

Constructs for Expression of SNG1 in *E. coli:*

Two oligonucleotides were designed to amplify a fragment of the SNG1 cDNA encoding a protein devoid of the first nineteen amino acids of a predicted signal peptide and to create a fragment suitable for cloning, in frame, into the pET28A expression vector (Novagen). The N-terminal oligonucleotide 5'-TCATGACCTCTATCGTCAAGTTTCTTCC-3' (SEQ ID NO:2) incorporates a start codon and the restriction site PagI (TCATGA) (SEQ ID NO:3) and alters the N-terminal alanine codon (GCC) to a threonine codon (ACC). The C-terminal oligonucleotide 5'-GTCGACTTACAGGGGTTGGCCACTG-3' (SEQ ID NO:4) incorporates a SalI restriction site after the stop codon. The SNG1 gene was amplified from DNA of the SMT cDNA clone (SEQ ID NO:5). Conditions for a 100 μL PCR reaction were: 50 mM KCl, 10 mM Tris/HCl (pH 9), 0.1% Triton X-100, 2.5 mM $MgCl_2$, 0.2 mM dNTPs, 1 μM oligonucleotides, 5 units Taq DNA polymerase (MBI Fermentas, USA), 10 ng cDNA plasmid template, 1.5 min 94° C., 1.5 min 55° C., 2.5 min 72° C., 25 cycles. The sequence modifications introduced through the PCR primers (SEQ ID NO:2 and SEQ ID NO:4) generated a SMT gene with the nucleotide sequence listed in SEQ ID NO:6 and its predicted amino acid sequence (SEQ ID NO:7). The products of the PCR were cloned into a pSKII+ vector (Stratagene, USA) and sequenced. The SNG1 gene was excised by PagI-SalI digestion and cloned into the NcoI-SalI digested pet28A vector to yield pet28A-SNG1. The *E. coli* host BL21DE3 was transformed with the empty pET28A vector and pET28A-SNG1.

Figure 3:
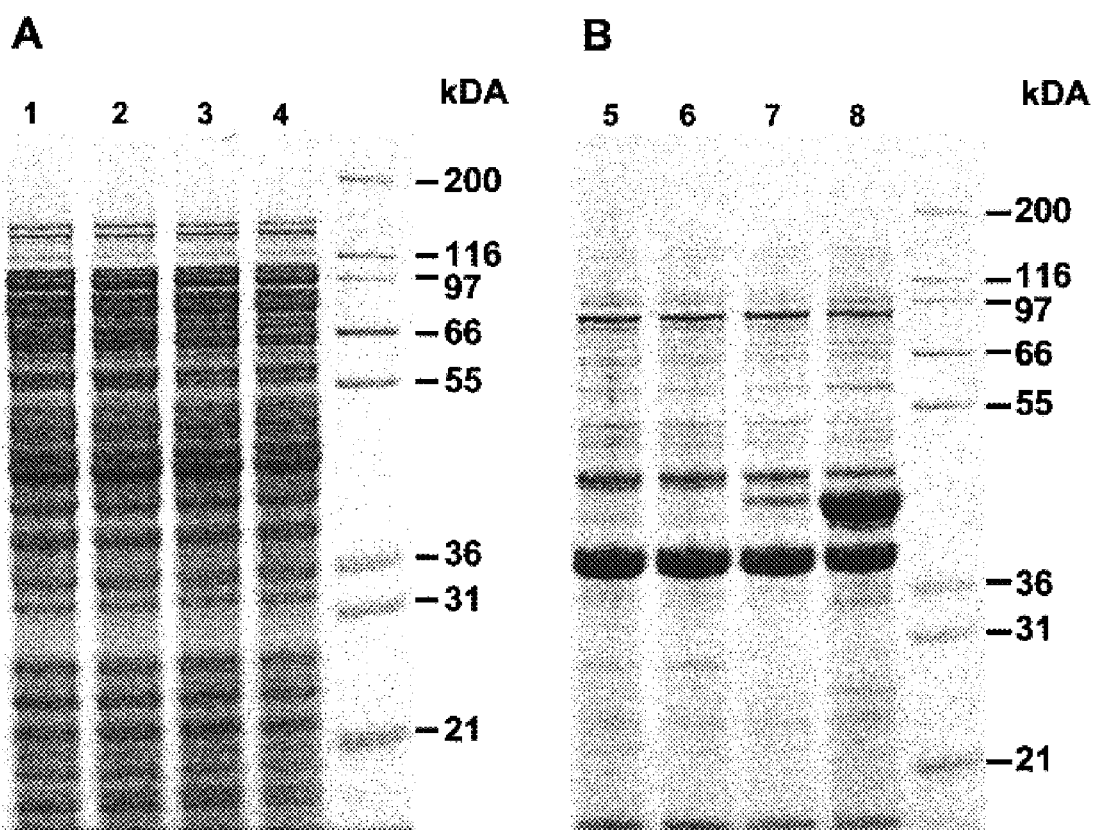
FIG. 3 shows an electrophoresis gel comparing the proteins isolated from a soluble and insoluble cell fraction from recombinant E. coli expression SNG1.

*E. coli* growth conditions and preparation of *E. coli* extracts:

An overnight culture of bacteria grown at 37° C. was diluted 200 fold into fresh LB medium and grown at 18° C. to an $OD_{600\ nm}$ of 0.6. Cells were subsequently induced with 0.8 mM IPTG and grown for 48 h at 14° C. Cells were harvested and lysed in 2.5 mL of 20 mM Tris/HCl pH 8, 500 mM NaCl using a french press. The cell lysate was cleared by centrifugation at 14,000 g at 4° C. for 30 min. Supernatant (soluble protein fraction) and pellet (insoluble protein fraction) were analyzed by PAGE as shown in FIG. 3. Protein concentration of the soluble fraction was determined using the Bradford assay. FIG. 3 shows the SDS PAGE analysis of soluble (A) and insoluble (B) fractions of *E. coil* harboring pET28A (lanes 1, 2, 5 and 6) and the SNG1 expression vector pET28A-SNG1 (lanes 3, 4, 7 and 8). Furthermore, lanes 1, 3, 5 and 7 contain protein of *E. coli* grown in the absence of IPTG and lanes 2, 4, 6 and 8 contain protein of *E. coli* cells grown in the presence of 0.8 mM IPTG.

Figure 4:
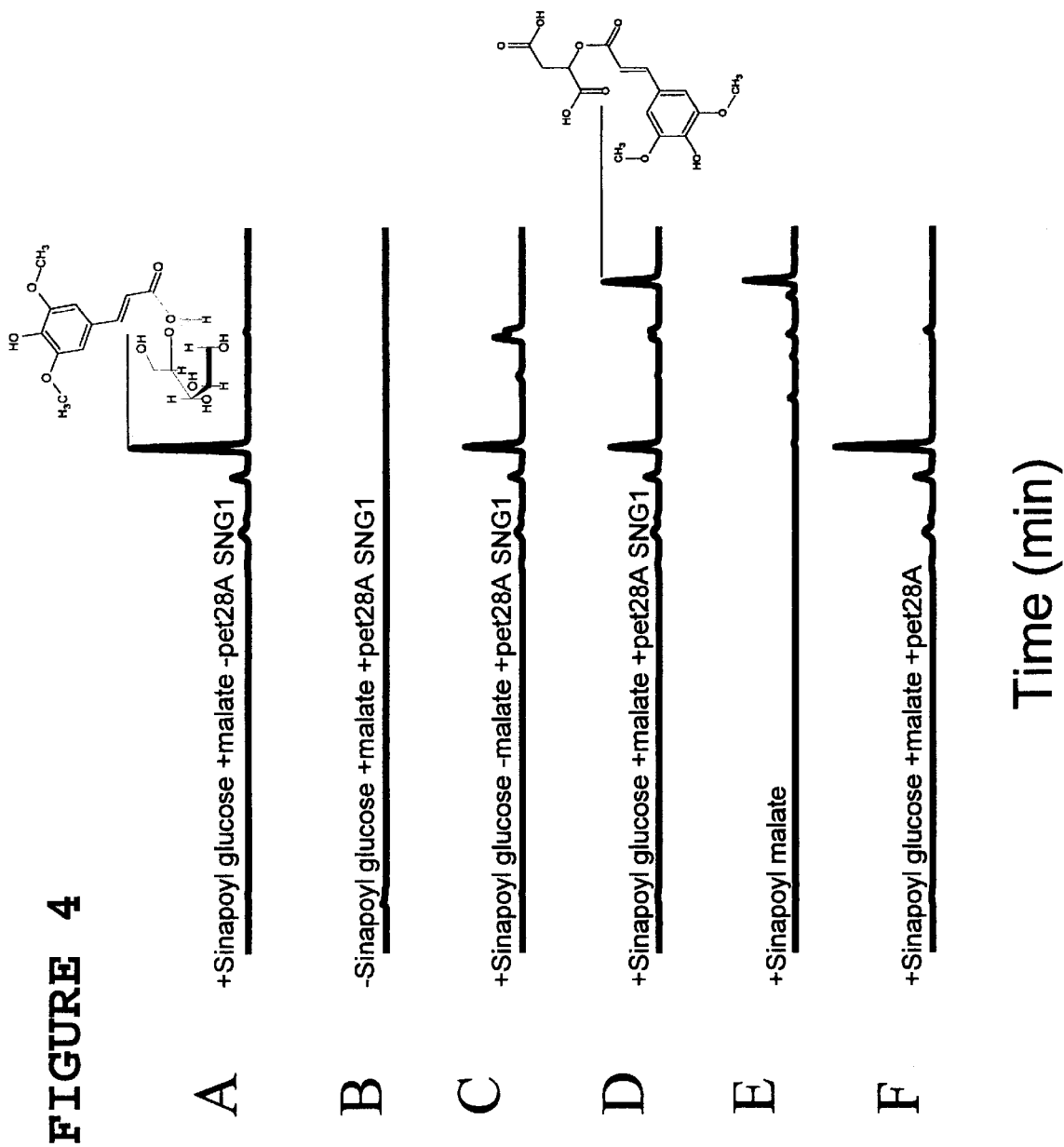
FIG. 4 is a plot of retention peaks from HPLC analysis of SMT assays of E. coli protein extracts.

When expressed in the *E. coli* cytoplasm the SNG1 gene product had a pronounced tendency to accumulate as an insoluble, misfolded and inactive inclusion body protein. However partitioning of active SMT into the cytoplasmic, soluble fraction could be improved by growing the *E. coli* cells at low temperatures (14° C.) and reducing the level of gene expression through omission of IPTG in the growth medium. The soluble protein fraction of *E. coli* cells harboring the SNG1 expression construct (SEQ ID NO:6) contained an enzymatic activity that was able to convert sinapoyl glucose to sinapoyl malate. Enzyme assays were analyzed by HPLC as described in the General Methods and results are shown in FIG. 4. As shown in FIG. 4, assays were incubated at 30° C. for 14 h; A) without protein; B) with 100 μg of soluble protein of *E. coli* harboring pET28A-SNG1 without sinapoyl glucose (sg); C) with 100 μg of soluble protein of *E. coli* harboring pET28A-SNG1 without malate; D) with 100 μg of soluble protein of *E. coli* harboring pET28A-SNG1 with both substrates; E) methanol extract of Arabidopsis leaves containing sinapoyl malate (sm); F) with 100 μg of soluble protein of *E. coli* harboring pET28A with both substrates. The analyzed protein extracts were obtained from cultures that had not been induced with IPTG. In vitro production of the compound that co-eluted with authentic sinapoyl malate isolated from Arabidopsis leaf material was dependent on the presence of the SMT gene and the presence of both substrates, malate and sinapoyl glucose. This experiment provides unequivocal proof that the SMT encodes a protein with sinapoylglucose:malate sinapoyl transferase (SMT) activity.

Isolation and Purification of the SMT Inclusion Body Protein:

SMT protein was obtained by purification from *E. coli* inclusion bodies. A single colony of the *E. coli* host BL21DE3 harboring the pet28A-SNG1 construct was used to inoculate a 5 mL culture of fresh LB medium containing 50 mg/L kanamycin. The culture was grown to stationary phase overnight at 37° C. This culture was diluted 200 fold into 500 mL LB supplemented with kanamycin 50 mg/L. The initial $OD_{600}$ was taken (0.024) and then checked each subsequent hour (1 h 0.017; 2 h 0.020; 3 h 0.151; 4 h 0.389) until the $OD_{600}$ was between 0.4 and 0.6. At this point, the culture was supplemented with IPTG (final concentration 1 mM) to induce production of the recombinant protein. After 3 h of induction, the cells were spun at 7,000 rpm for 10 min. The cells were resuspended in 25 mL Lysis Buffer (25 mM Tris/Ac pH 7.5, 1 mM EDTA, 0.1% Triton X-100, 0.1 mg/mL lysozyme, 0.01 mg/mL RNAseA, 0.05 mg/mL DNAseI, and 2 mM $MgCl_2$) and incubated 10 min on ice. The insoluble fraction was pelleted at 12,000 rpm for 10 min and washed 3 times in 10 mL 1 st Wash Buffer (50 mM Tris/HCl pH 7.7, 0.3 M NaCl, 1 mM EDTA, 0.1% Triton X-100). The pellet was washed with 5 mL 2nd Wash Buffer (1St Wash Buffer+5 mM DTT) and finally resuspended in 1.5 mL 2nd Wash Buffer+5% glycerol. The protein was quantitated on a PAGE gel using serial dilutions of the inclusion body suspension. The protein was stored at −80° C.

Refolding of SMT in vitro:

Isolated *E. coli* inclusion bodies (~1.15 mg of total protein), consisting primarily of recombinant mature Arabidopsis SMT and some minor protein contaminants, were resuspended in 0.64 mL of a solution containing 8 M urea, 100 mM Tris-HCl (pH 8), 1 mM EDTA, 20 mM dithiothritol. To facilitate dissolution of the pellet and ensure complete denaturation and reduction of the inclusion body material, the above sample was incubated for two h at room temperature with occasional vortex mixing. The solubilized inclusion bodies were then diluted 5-fold with a solution containing 8 M urea, 100 mM Tris-HCl (pH 8), 1 mM EDTA to a final protein concentration of ~0.36 mg/mL. The purpose of this step was to reduce the concentration of dithiothreitol in the subsequent folding reaction which would otherwise interfere with the reduced/oxidized glutathione-mediated oxido-shuffling conditions that are necessary for correct folding and disulfide bond formation of recombinant SMT. Following denaturation, protein folding was initiated using the so-called rapid dilution technique (Rudolph et al., *FASEB J* 10(l):49–56 (1996)). An aliquot (0.4 mL) of the solubilized inclusion body mixture was slowly added to a 250-mL glass beaker (dropwise, over the course of several minutes) that contained a magnetic stir bar and 100 mL of folding buffer. The latter consisted of 100 mM Tris-HCl (pH 8), 0.2 mM EDTA, 15% (v/v) glycerol, 0.01% (v/v) Tween- 20 (BioRad, USA, catalog number 170-6531), 3 mM reduced glutathione and 0.6 mM oxidized glutathione at room temperature. To ensure rapid dilution of the chaotrope, the solution in the beaker was vigorously stirred while the denatured protein was added, although care was taken to minimize frothing. After eight such additions were made to the same reaction vessel at ~15 min intervals, the mixture was incubated for 16 h at room temperature (without stirring) to allow the folding reaction to reach completion.

The first step in the purification of active recombinant SMT involves anion exchange chromatography. Unless otherwise stated, all steps were performed at room temperature. The 100 mL folding reaction was applied in aliquots to a 25 mL plastic disposable column (Bio-Rad, Hercules, Calif.) that contained 2 mL (settled bed volume) of Q-Sepharose Fast Flow (Pharmacia, Piscataway, N.J.) that was equilibrated with Buffer 1 (50 mM Tris-HCl (pH 8), 0.1 mM EDTA, 15% (v/v) glycerol, 0.01% (v/v) Tween-20). After allowing the entire sample to pass through the column by gravity, the resin was washed twice with 3 mL of Buffer 1 that also contained 0.1 M NaCl and the eluent was discarded. Active recombinant SMT was then recovered from the column using 0.2 M NaCl in Buffer 1. The resin was washed twice with 3 mL of this solution and the combined eluents were stored at −80° C. for subsequent processing. Approximately 78% of the SMT enzyme activity that was present in the original 100 mL folding reaction was recovered in the 0.2 M NaCl washes. The 6 mL fraction containing active SMT was then concentrated at 4° C. to 230 $\mu$L using a Centricon-10 (Amicon, Danvers, Mass.) according to the manufacturer's instructions, and 200 $\mu$L of this material was applied to a 7.5×600 mm TSK G3000SW gel-filtration column (Toso Haas, Montgomeryville, Pa.). The column was equilibrated at room temperature at flow a rate of 1 mL/min with 50 mM Tris-HCL (pH 7.5), 0.3 M NaCl, 15% (v/v) glycerol, 0.1% (v/v) Tween-20. The material eluting from the column between 15.7–18 min (i.e. the major peak absorbing at 280 nm) was collected, concentrated to 100 $\mu$L using a Centricon-10, and frozen at −80° C. for subsequent use. The recovery of SMT activity from the gel filtration step was ~52% of that applied to the column.

As judged by SDS-PAGE and Coomassie-blue staining, the folded recombinant protein was at least 80% pure and the final yield of active SMT from the 100 mL folding reaction was ~6 $\mu$g, corresponding to ~0.52% of the original inclusion body material. The turnover number for purified recombinant SMT folded from inclusion bodies was ~18/sec at 30° C., which compares favorably to the 11.5/sec value that was previously reported for the authentic protein purified from radish (Graewe et al., *Planta* 187:236–241 (1992)). For this determination the 25 $\mu$L enzyme reaction contained 100 mM potassium phosphate buffer (pH 6.2), 500 $\mu$M sinapoyl glucose and 200 mM L-malate. Although native Arabidopsis SMT has not yet been purified to homogeneity and its turnover number remains to be determined, the above observations suggest that the purified recombinant protein described above is probably fully active.

Example 2

SMT Protein Required for Conjugation of Benzoic Acids with Malate

A construct for ectopic overexpression of the chorsimate-pyruvate lyase gene of *E. coli* (described in the General Methods) was introduced into wildtype and sng1-1 (Lorenzen et al., *Plant Physiology* 112:1625–1630(1996)) mutant plants of *Arabidopsis thaliana*. The sng1-1 mutant of *Arabidopsis thaliana* is known to be deficient in SMT activity (Lorenzen et al., *Plant Physiology* 112:1625–1630 (1996)). The binary vector carrying the CPL expression cassette was transformed into *Agrobacterium tumefaciens* strain C58 C1 Rif$^R$ (also known as strain GV3101), carrying the disarmed Ti (virulence) plasmid pMP90 (Koncz and Schell, *Mol. Gen. Genet.* 204:383–396 (1986)) (this strain/plasmid combination will hereafter be referred to as strain MP90) by electroporation, using available protocols (Meyer et al., *Science* 264:1452–1455 (1994)). The MP90 strain carrying the binary vector with the CPL expression construct was used to transform *Arabidopsis thaliana* using a published protocol of the in planta transformation technique (Clough et al., *Plant J.* 16(6):735–43 (1998)). Transgenic seedlings were identified under sterile conditions on standard plant growth media (Murashige et al., *Physiol. Plant.* 15:473–497 (1962)) using 50 mg/L kanamycin (Sigma, USA) as a selectable agent. About 300 kanamycin resistant seedlings ($T_1$ generation) were transferred to soil and grown at 21° C., 60% relative humidity and a 14 h light/10 h darkness cycle until seed could be harvested. Seeds of the $T_2$ generation were germinated on selective media. Fifteen seedlings of seven independent transformed lines of wildtype and sng1-1 genetic background were transferred to soil and grown as described above. Seeds from $T_2$ plants were harvested individually and germinated on selective media. Seed batches that did not segregate kanamycin-sensitive progeny indicated that the parent plant was homozygous for the inserted T-DNA. Plants derived from these homozygous seed batches were grown in soil for 28 d.

Analysis of PHBA Conjugates:

About 20 mg of leaf tissue of each line was extracted with 100 $\mu$L of 50% methanol, 0.75% phosphoric acid. Leaf tissue was homogenized using a plastic pestle. The leaf homogenate was cleared by centrifugation. The methanol extract was analyzed by HPLC on a Nova-Pak® C18 column (60 A pore size, 4 $\mu$M particle size) (Waters, USA) using a gradient from 6% acetonitrile, 1.5% phosphoric acid (solvent A) to 48% acetonitrile, 1.5% phosphoric acid (solvent B) and UV detection at 254 nm. The following solvent gradient was applied: 0–5 min 100% solvent A; 20 min 100% solvent B; 21–25 min 100% solvent A. The PHBA conjugates were detected at 254 nm absorbance wavelength and quantitated using calibration curves generated with chemically synthesized standard compounds of 1-O-phenol and 1-O-acyl glucosides of PHBA (described in the General Methods). Standards of PHBA malate were generated through enzymatic conversion of known quantities of the 1-O-acyl glucoside of PHBA using the recombinantly produced SMT protein (see Example 1).

Figure 5:
FIG. 5 shows HPLC traces of methanolic leaf extracts of transgenic Arabidopsis plants expressing the chorismate pyruvate-lyase (CPL) gene of E. coli.

FIG. 5 shows HPLC traces (measured at 254 nm absorbance wavelength) of methanolic extracts of wildtype and sng1-1 Arabidopsis plants expressing the CPL gene. Results show that wildtype plants produce a compound that absorbs at 254 nm that is missing in the sng1-1 mutant and in plants lacking the CPL transgene. The novel compound was analyzed by LC/MS as described in the General Methods. The compound produced a molecular ion in electrospray negative ionization mode that exhibited a mass to charge ratio (m/z-) of 253.15 that is in very close agreement with the expected m/z- of PHBA malate (MW 254.193). Table 1 displays the concentration of PHBA conjugates in wildtype and sng1-1 mutant Arabidopsis plants expressing the CPL gene.

TABLE 1

|  | PHBA 1-O-Phenol Glucoside (µmoles/g dry weight) | PHBA 1-O-Acyl Glucoside (µmoles/g dry weight) | PHBA L-Malate Ester (µmoles/g dry weight) |
| --- | --- | --- | --- |
| Arabidopsis wildtype | n.d | n.d. | n.d. |
| Arabidopsis wildtype CaMV35S CPL A | 50.7 | 46.0 | 37.2 |
| Arabidopsis wildtype CaMV35S CPL B | 88.3 | 150.3 | 60.0 |
| Arabidopsis wildtype CaMV35S CPL C | 71.3 | 96.9 | 56.4 |
| Arabidopsis wildtype CaMV35S CPL D | 57.4 | 70.4 | 35.1 |
| Arabidopsis wildtype CaMV35S CPL E | 59.4 | 86.0 | 39.0 |
| Arabidopsis wildtype CaMV35S CPL F | 115.5 | 144.8 | 68.4 |
| Arabidopsis wildtype CaMV35S CPL G | 66.1 | 94.2 | 52.5 |
| Arabidopsis sng1-1 CaMV35S CPL H | 47.0 | 67.0 | n.d. |
| Arabidopsis sng1-1 CaMV35S CPL I | 45.2 | 81.0 | n.d. |
| Arabidopsis sng1-1 CaMV35S CPL J | 48.1 | 75.3 | nd. |
| Arabidopsis sng1-1 CaMV35S CPL K | 21.4 | 28.9 | n.d. |
| Arabidopsis sng1-1 CaMV35S CPL L | 35.6 | 57.6 | n.d. |
| Arabidopsis sng1-1 CaMV35S CPL M | 65.7 | 90.2 | n.d. |
| Arabidopsis sng1-1 CaMV35S CPL N | 32.4 | 36.8 | n.d. |

PHBA malate levels were below detection limit (not detected-n.d.) in all seven sng1-1 lines analyzed, whereas PHBA malate was present in transgenic plants of the wildtype background.

Example 3

PHBA 1-O-acyl Glucoside is a Substrate of SMT in in vitro Reactions

Figure 6:
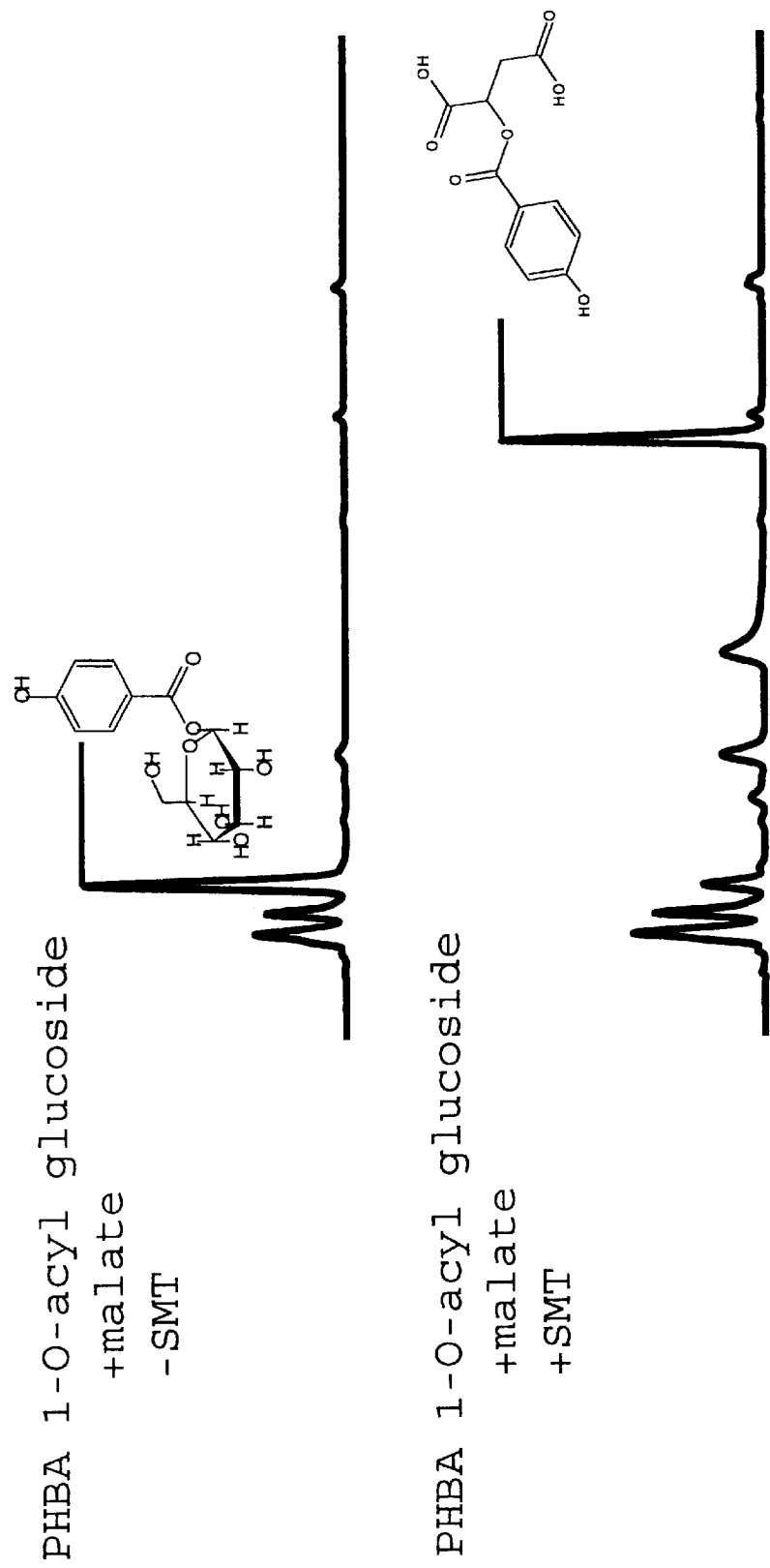
FIG. 6 shows HPLC analysis of enzyme assays performed with recombinantly produced, refolded SMT enzyme using L-malate and pHBA 1-O-acyl glucoside as substrates.

Approximately 250 ng of recombinantly produced, refolded SMT protein was incubated with 200 mM malate, 0.1 mM PHBA 1-O-acyl glucoside in a 25 µL reaction in 100 mM potassium phosphate buffer (pH 6.2) for 12 h at 30° C. Reaction products were separated by HPLC as described in the General Methods. FIG. 6 shows HPLC traces of the reaction products obtained with PHBA 1-O-acyl glucoside and malate in the absence or presence of the refolded recombinantly produced SMT protein. In the presence of the SMT enzyme, the PHBA 1-O-acyl glucoside is converted to a new compound with an retention time different from that of the glucose conjugates of PHBA. The compound was analyzed by LC-MS as described in the General Methods. By LC/electrospray MS, the compound produces a molecular ion in negative ionization mode that exhibits a mass to charge ratio (m/z-) of 253.37 that is in very close agreement with the expected m/z- of PHBA malate (MW 254.193). The MS spectrum of the compound closely matches that of the compound isolated from wildtype Arabidopsis plant expressing the CPL gene. These examples have shown that PHBA malate is produced from the PHBA 1-O-acyl glucoside and L-malate both in vivo and in vitro through the action of the SMT enzyme.

Example 4

Comparison of Catalytic Properties of SMT with Benzoic and Hydroxycinnamic Acid Substrates Large Scale Folding of SMT 35 mg of purified SMT inclusion body protein were refolded in a one-liter folding reaction essentially as described in Example 1. SMT activity was purified by anion exchange chromatography on 8 mL of fast flow Q-Sepharose (Pharmacia, USA). Approximately 120 µg of active SMT protein was eluted from the Q-Sepharose column.

Determination of $K_m$ and $V_{max}$:

Sinapoyl Glucose

Rates of sinapoyl malate synthesis were determined at 30° C. in enzyme assays (100 µL) that consisted of 200 mM malate (pH 6.0) in 100 mM potassium phosphate buffer (pH 6.8), 50 ng of partially purified SMT protein and sinapoyl glucose at 2760, 500, 250, 125, 57, 29, 14 and 6.6 µM. Sinapoyl malate synthesis was measured after 5, 10, 20 and 30 min using HPLC as described above. Its $K_m$ was determined using the Hofstee plot by plotting velocity/substrate concentration versus velocity. In this plot an estimate of the $K_m$ is provided as the slope of the line representing the linear regression curve through all points. The $K_m$ of SMT for sinapoyl glucose was determined to be about 541 µM. Furthermore, using the y-intercept of the regression curve, the $V_{max}$ of SMT for sinapoyl glucose was estimated to be 21.315 µmol min$^{-1}$ mg$^{-1}$ protein.

Malate

Rates of sinapoyl malate synthesis were determined at 30° C. in enzyme assays (100 µL) that consisted of 500 µM sinapoyl glucose (pH 6.0) in 100 mM potassium phosphate buffer (pH 6.8), 50 ng of partially purified SMT protein and malate at 200, 100, 50, 25, 12.5, 6.25, 3.125 and 1.5625 mM. Sinapoyl malate synthesis was measured at 3, 6, 12 and 24 min using HPLC as described above. Its $K_m$ was determined using the Hofstee plot by plotting velocity/substrate concentration versus velocity. In this plot an estimate of the $K_m$ is provided as the slope of the line representing the linear regression curve through all points. The $K_m$ of SMT for malate was determined to be about 42 mM.

PHBA 1-O-acyl Glucoside

Rates of PHBA malate synthesis were determined at 30° C. in enzyme assays (100 µL) that consisted of 200 mM malate (pH 6.0) in 100 mM potassium phosphate buffer (pH 6.8), 500 ng of partially purified SMT protein and PHBA 1-O-acyl glucoside at 5680, 2884, 1517, 743, 365, 195, 94 and 48 µM. PHBA malate synthesis was measured after 45, 90, 120 and 240 min using HPLC as described above. Its $K_m$ was determined using the Hofstee plot by plotting velocity/substrate concentration versus velocity. In this plot an estimate of the $K_m$ is provided as the slope of the line representing the linear regression curve through all points. The $K_m$ of SMT for PHBA 1-O-acyl glucoside was determined to be about 354 µM. Furthermore, using the y-intercept of the regression curve the $V_{max}$ of SMT for PHBA 1-O-acyl glucoside was estimated to be 0.2482 µmol min$^{-1}$ mg$^{-1}$ protein.

Example 5

SMT Accepts other α-Hydroxy Carboxylic Acids as Substrates

Figure 7:
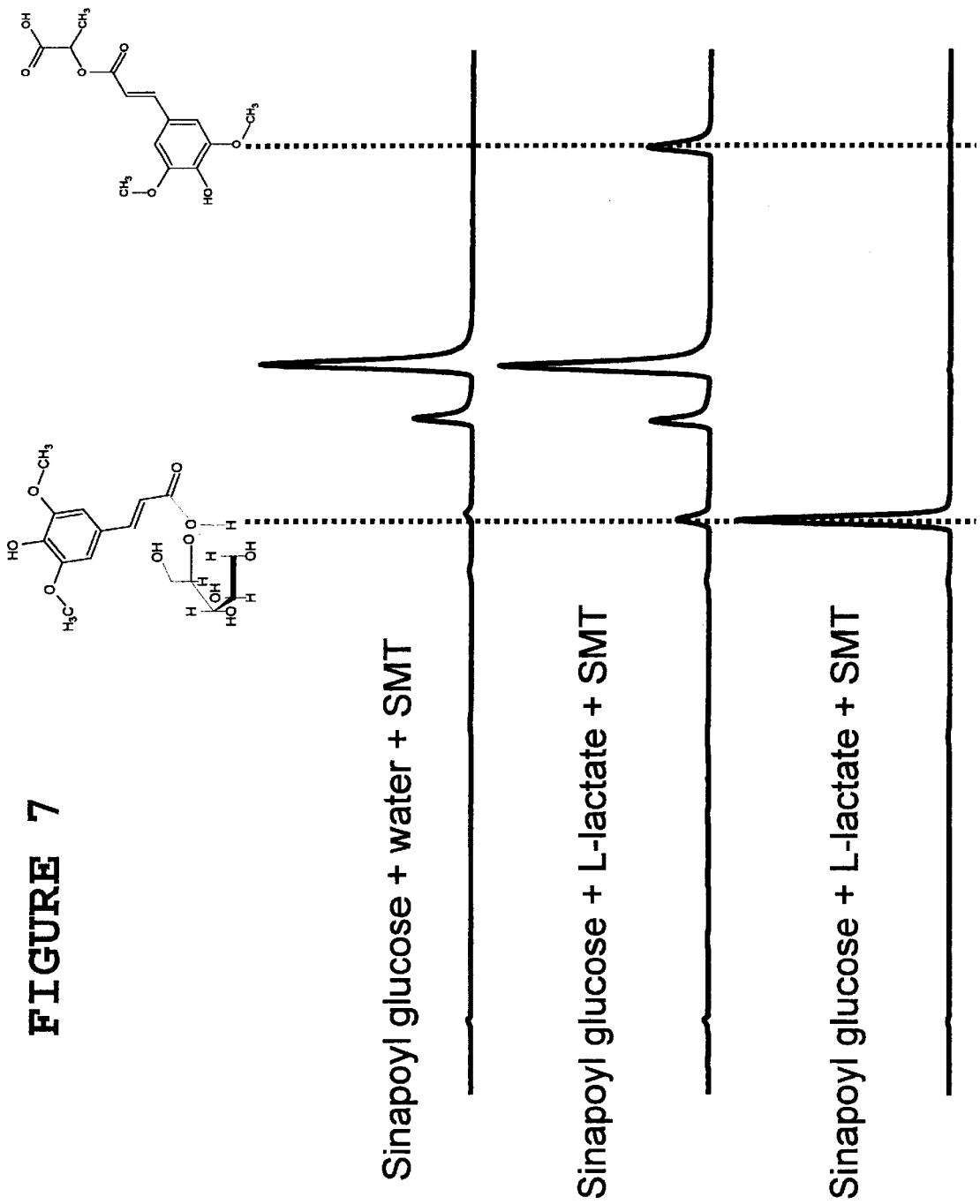
FIG. 7 shows HPLC analysis of enzyme assays performed with recombinantly produced, refolded SMT enzyme using L-lactate and sinapoyl glucose as substrates.

The activity of the SMT enzyme was determined using sinapoyl glucose and L-lactate as follows. 1 µg of partially purified recombinant SMT protein was incubated with 500 µM sinapoyl glucose in 100 mM potassium phosphate buffer (pH 6.2) in the absence or presence of 200 mM L-lactate. Enzyme reactions were incubated at 30° C. for 12 h. Reaction products were analyzed by HPLC as described in the General Methods. FIG. 7 shows HPLC traces of reaction products generated with SMT and sinapoyl glucose in presence or absence of L-lactate. In the presence of L-lactate a new compound that absorbs at 335 nm is produced. Production of this compound is dependent on the presence of the SMT enzyme. When subjected to LC/electrospray MS, this compound produced a molecular ion of m/z-=295.0 that is in very close agreement with the expected m/z- of the molecular ion of sinapoyl lactate (MW 296.273). This example demonstrates that the SMT protein is able to accept α-hydroxycarboxylic acids other than L-malate in acyltransfer reactions that involve sinapoyl glucose.

Example 6

SMT Expression is Sufficient to Establish Malate Conjugation of PHBA in a Heterologous Plant Construction of a Transformation Vector A variant of the SMT gene (SEQ ID NO:9) was amplified from the SMT cDNA plasmid using the oligonucleotide primers 5'-GAGAATATCATGAGTTTGAAAATAAAG-3' (SEQ ID NO:8) and 5'-GTCGACTTACAGGGGTTGGCCACTG-3' (SEQ ID NO:4) using the following conditions: 50 mM KCl, 10 mM Tris/HCl pH 9, 0.1% Triton X-100, 2.5 mM $MgCl_2$, 0.2 mM dNTPs, 1 μM oligonucleotides, 5 Units Taq DNA polymerase (MBI Fermentas, USA), 10 ng cDNA plasmid template, 1.5 min 94° C., 1.5 min 55° C., 2.5 min 72° C., 25 cycles. PCR products were cloned into pSKII. An *E. coli* clone was identified that contained a recombinant plasmid in which the 5' region of the SMT gene was proximal to the T7 promoter of the pSKII+ vector. The SMT gene was excised from this plasmid by HincII SstI digestion. A derivate of the CaMV35S promoter (Odell et al., *Nature* 313:810–812 (1985)) was excised from pBI121 (Jefferson et al., *EMBO J.* 13:3901–3907 (1987)) by digestion with HindIII and SmaI. The CaMV35S promoter was fused to the SMT gene by a three way ligation to the HindIII SstI digested pSKII+ vector. The CaMV35S SMT expression cassette was excised from pSKII+by HindIII SstI double digestion and ligated to the HindIII SstI digested pGPTV-Hyg vector (Becker et al., *Plant Mol. Biol.* 20:1195–1197 (1992)) to give pGPTV-HYG-SMT. This vector functions as a binary vector in Agrobacterium tumefaciens-mediated plant transformation and provides the polyadenylation signal of the nopaline synthase gene downstream of the SMT gene. The pGPTV-HYG-SMT construct and the unaltered pGPTV-Hyg vector were introduced into *Agrobacterium tumefaciens* C58 MP90 by electroporation as described above.

Transformation of Tobacco

*Agrobacterium tumefaciens* cultures harboring the pGPTV-HYG-SMT and pGPTV-Hyg were employed to transform a tobacco plant that expressed the CPL gene of *E. coli* (described in the General Methods). Previous analyses indicated that as result of CPL expression this plant produces between 5–7% of its dry weight in the form of 1-O-phenol and 1-O-acyl glucoside of PHBA (described in the General Methods). Transgenic tobacco plants harboring the CPL gene and a transgene derived from either the empty pGPTV-Hyg (8 transgenic lines) or the pGPTV-HYG-SMT construct (59 transgenic lines) were generated essentially as described by Horsch et al., (*Science* 227:1229–1231 (1985)) using selective media containing 30 mg/L hygromycin B (Gibco BRL, USA).

Analysis of SMT Activity in Tobacco

SMT acitvity could be detected in two trangenic tobacco plants (Line H8-4 and H9-1) harboring the SMT T-DNA derived from the pGPTV-HYG-SMT construct. 50 mg of leaf tissue was homogenized in 250 μL of 100 mM potassium phosphate buffer (pH 6.2) containing 10% (w/v) polyvinylpolypyrolidone (PVPP). The extract was cleared by centrifugation. Its protein concentration was estimated using the Bradford method (Bradford et al., *Anal. Biochem.* 1976:341–376 (1976)). Approximately 50 μg of protein was assayed for SMT activity as described in the General Methods.

Table 2 shows that CaMV35 promoter mediated expression of SMT in tobacco leads to presence of SMT activity in leaf extracts.

TABLE 2

| Plant | Transgene | SMT activity (nmol sinapoyl malate/min/mg protein) |
|---|---|---|
| Arabidopsis 10d | — | 7.0 |
| Arabidopsis 28d | — | 11.3 |
| Tobacco H10-3 42d | CaMV35S CPL | not detected |
| Tobacco H9-1 young leaf 42d | CaMV35S CPL/SMT | 1.4 |
| Tobacco H9-1 old leaf 42d | CaMV35S CPL/SMT | 2.1 |
| Tobacco H8-4 young leaf 42d | CaMV35S CPL/SMT | 2.1 |
| Tobacco H8-4 old leaf 42d | CaMV35S CPL/SMT | 8.5 |

Specific SMT activity in extracts of plants harboring the pGPTV-HYG-SMT derived transgene is comparable to specific activity in wildtype Arabidopsis plants and SMT activity is absent in tobacco plants that only carry the pGPTV-Hyg derived transgene (Line H10-3). To date SMT enzyme activity has only been detected in cruciferous plant species such as *Arabidopsis thaliana, Raphanus sativus* or *Brassica rapa* (Strack, D., *Planta* 155:31–36 (1982); Mock et al., *Z. Naturforsch.* 47c:680–682 (1992)). In these plants the SMT enzyme is targeted to the vacuole of the plant cell (Sharma V. and Strack, D., *Planta* 163:563–568 (1985)). This example demonstrates that the SMT gene can be introduced into a heterologous non-cruciferous plant species and that as result of SMT gene expression active SMT enzyme is produced.

Analysis of PHBA Conjugates in Tobacco

Figure 8:
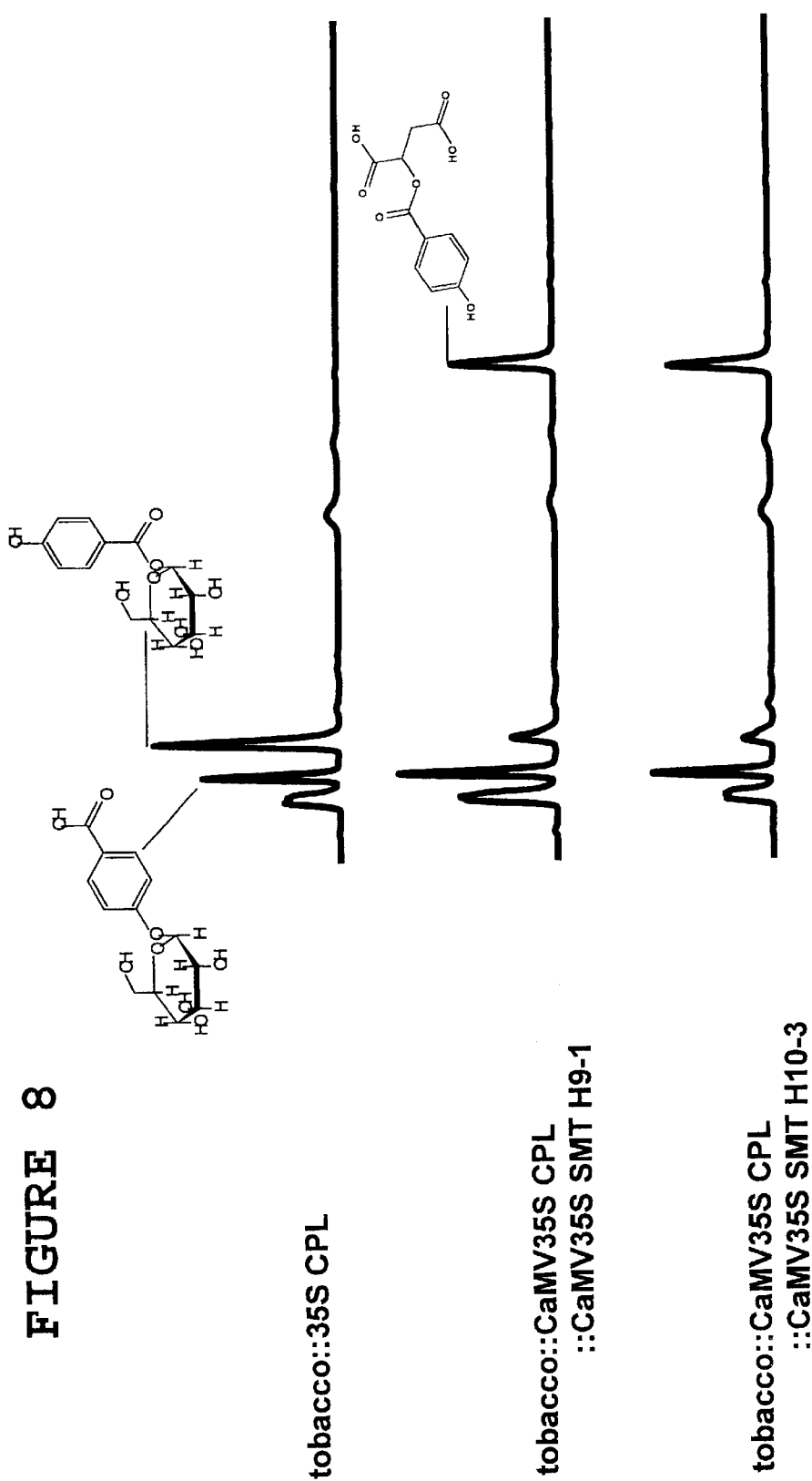
FIG. 8 shows HPLC traces of methanolic leaf extracts of transgenic tobacco plants expressing the chorismate pyruvate-lyase (CPL) gene of E. coli alone or together with the SMT gene.
Figure 9:
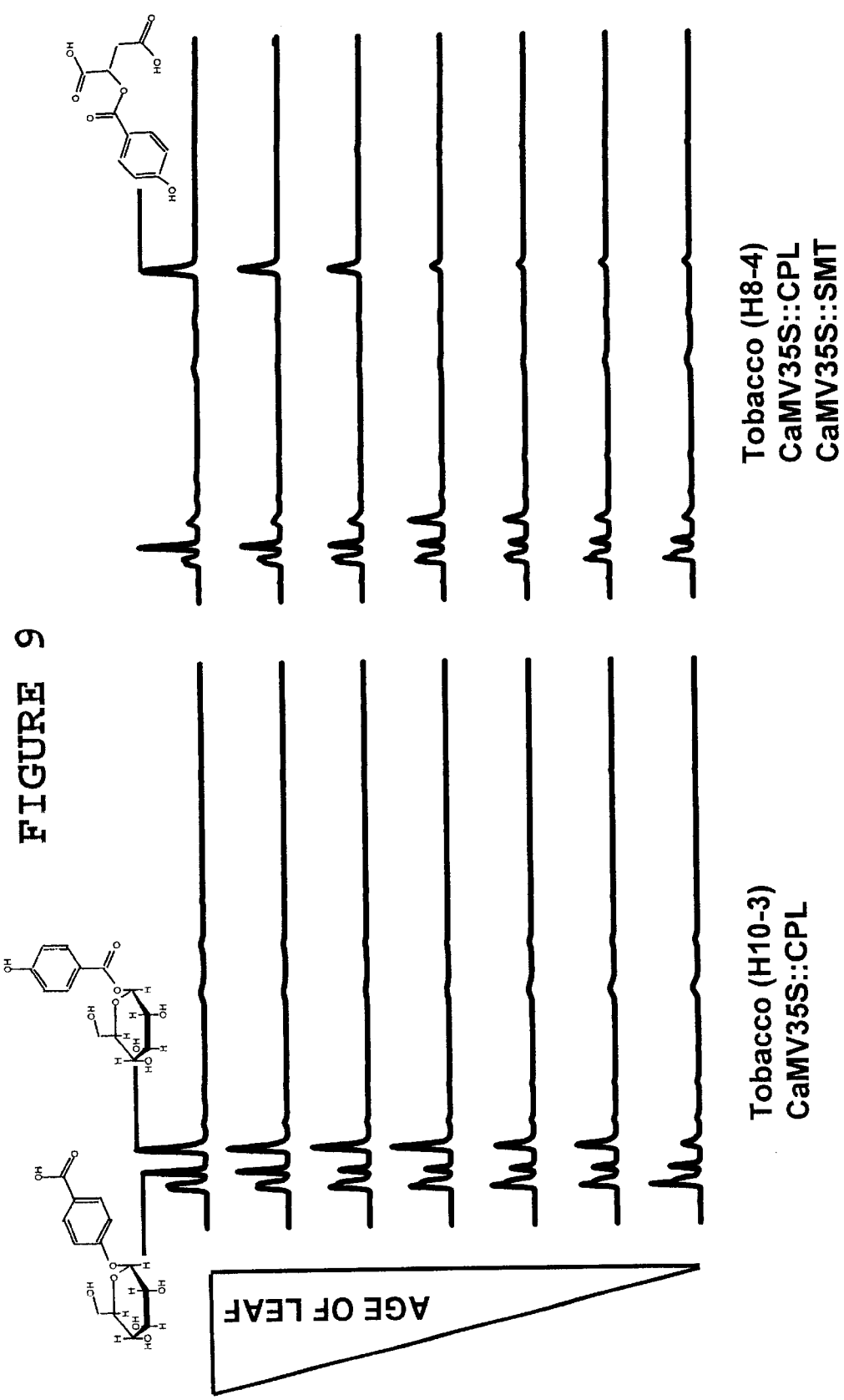
FIG. 9 shows changes in the relative abundance of pHBA conjugates in leaves of different age in lines H10-3 and H8-4.

HPLC analysis was employed to detect PHBA conjugates in tobacco harboring either the CaMV35S CPL transgene and the pGPTV-Hyg (line H10-3) or CaMV35S CPL transgene and the pGPTV-Hyg-SMT transgene (line H8-4, H9-1). Tissue was extracted from plants six weeks after transfer to soil. FIG. 8 shows that line H8-4 and line H9-1 contain a new compound that is absent for H10-3. Presence of this compound is accompanied by a dramatic reduction in the amount of 1-O-acyl glucoside of PHBA. This compound was subjected to LC/electrospray MS analysis as described in the General Methods. Furthermore, this compound produces a molecular ion in electrospray negative ionization mode that exhibits a mass to charge ratio (m/z-) of 253.02 that is in very close agreement with the expected m/z- of PHBA malate (MW 254.193). The fragmentation pattern of the compound is indistinguishable from that of the putative PHBA malate molecule isolated from Arabidopsis wildtype plants expressing the CPL gene and of the compound synthesized in vitro using the recombinantly produced SMT protein using 1-O-acyl glucoside of PHBA and malate. FIG. 9 shows changes in the relative abundance of PHBA conjugates in leaves of different age in lines H10-3 and H8-4. Leaf samples were harvested from plants six weeks after transfer to soil. Seven leaves were sampled starting with the youngest leaf close to the plant apex. It is apparent that as a result of constitutive SMT expression the 1-O-acyl glucoside of PHBA only transiently accumulates and is later converted to PHBA malate. In older leaves of line 8-4 harboring CPL and SMT transgene the 1-O-acyl glucoside of PHBA is almost quantitatively converted to PHBA malate.

PHBA conjugate levels were measured in lines H10-3 and H8-4 3 a month after transfer to soil. Sixteen different leaves were sampled from each plant. PHBA conjugate levels were determined as described in Example 2. H10-3 contained PHBA 1-O-phenyl glucoside (165.4+/−37.7 μmol/g dry weight) and PHBA 1-O-acyl glucoside (80.0+/−17.3 μmol/g dry weight). H8-4 contained PHBA 1-O-phenyl glucoside (189.9+/−52.9 μmol/g dry weight), PHBA 1-O-acyl glucoside (19.3+/−8.2 μmol/g dry weight) and PHBA malate (83.7+/−8.2 μmol/g dry weight).

In summary, this example demonstrates that expression of SMT in a heterologous plant provides active SMT protein that is very likely targeted to the vacuole where it acts upon the 1-O-acylglucoside of PHBA and transfers the acyl moiety to malate. It is furthermore apparent that there is sufficient malate in the tobacco vacuole to sustain a significant rate of PHBA malate biosynthesis in a plant that normally does not accumulate malate conjugates of phenylpropanoid molecules.

Example 7

SMT Accepts Primary Alcohols as Substrates and Can be Utilized for Production of Methyl and Ethyl or Isopropyl Esters of Hydroxycinnamic or Benzoic Acids Activity of the SMT enzyme was determined using sinapoylglucose or PHBA 1-O-acylglucoside and methanol, ethanol and isopropanol. Briefly, 200 ng of partially purified recombinantly produced SMT protein was incubated with 500 μM of the glucose ester of sinapic acid or PHBA in 100 mM potassium phosphate buffer (pH 6.2) in the absence or presence of 400 mM of the respective alcohols in 100 μL enzyme reactions. Enzyme reactions were incubated at 30° C. for 16 h. All reaction products were analyzed by HPLC as described in Example 1. Applicants observed production of methyl, ethyl and isopropyl esters of sinapic acid and PHBA when using methanol, ethanol and isopropanol respectively in enzyme reactions. Production of these compounds is dependent on the presence of both SMT enzyme and alcohol. LC/electrospray MS analysis of reaction products provided the following m/z- for the enzymatically synthesized compounds:

methyl sinapic acid: 237.19
ethyl sinapic acid: 251.21
isopropyl sinapic acid: 265.23
methyl PHBA: 151.11
ethyl PHBA: 165.12
isopropyl PHBA: 179.12

The m/z- of molecular ions of the esters found very close agreement with the expected m/z- of molecular ions of compounds with the following molecular weights:

methyl sinapic acid: 238.237
ethyl sinapic acid: 252.263
isopropyl sinapic acid: 266.29
methyl PHBA: 152.147
ethyl PHBA: 166.174
isopropyl PHBA: 180.2

Applicants have thus demonstrated that the SMT protein is able to accept primary alcohols in acyltransfer reactions that involve glucose esters of hydroxycinnamic or benzoic acids.

What is claimed is:

1. A method for the production of pHBA ester malate comprising:
   a) providing a host cell producing suitable levels of glycosylated pHBA;
   b) introducing into the host cell a nucleic acid molecule encoding sinapoylglucose:malate sinapoyltransferase selected from the group consisting of
      i.) An isolated nucleic acid molecule encoding a polypeptide having an amino acid sequence selected from the group consisting of SEQ ID NO:1 and SEQ ID NO:7;
      ii.) An isolated nucleic acid molecule encoding a polypeptide having at least 90% identity with an amino acid sequence selected from the group consisting of SEQ ID NO:1 and SEQ ID NO:7 and
      iii.) An isolated nucleic acid molecule that is complementary to 1 or 2
      wherein the sinapoylglucose:malate sinapoyltransferase catalyzes the substitution of a glucose moiety on the glycosylated pHBA with a malate moiety to form pHBA ester malate; and
   c) optionally recovering the pHBA ester malate.

2. A method according to claim 1 wherein the host cell is selected from the group consisting of bacteria, filamentous fungi and plants.

3. A method according to claim 2 wherein the host cell is selected from the group consisting of Aspergillus, Trichoderma, Saccharomyces, Pichia, Candida, Hansenula, Salmonella, Bacillus, Acinetobacter, Rhodococcus, Streptomyces, Escherichia and Pseudomonas.

4. A method according to claim 2 wherein the host cell is selected from the group consisting of soybean, rapeseed, sunflower, cotton, corn, tobacco, alfalfa, wheat, barley, oats, sorghum, rice, Arabidopsis, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees and forage grasses.

* * * * *

SEQUENCE LISTING

<160> NUMBER OF SEQ ID NOS: 19

<210> SEQ ID NO 1
<211> LENGTH: 433
<212> TYPE: PRT
<213> ORGANISM: Arabidopsis thaliana

<400> SEQUENCE: 1

Met Ser Leu Lys Ile Lys Phe Leu Leu Leu Val Leu Tyr His His
1               5                   10                  15

Val Asp Ser Ala Ser Ile Val Lys Phe Leu Pro Gly Phe Glu Gly Pro
            20                  25                  30

Leu Pro Phe Glu Leu Glu Thr Gly Tyr Ile Gly Ile Gly Glu Asp Glu
        35                  40                  45

Asn Val Gln Phe Phe Tyr Tyr Phe Ile Lys Ser Glu Asn Asn Pro Lys
    50                  55                  60

Glu Asp Pro Leu Leu Ile Trp Leu Asn Gly Gly Pro Gly Cys Ser Cys
65                  70                  75                  80

Leu Gly Gly Ile Ile Phe Glu Asn Gly Pro Val Gly Leu Lys Phe Glu
                85                  90                  95

Val Phe Asn Gly Ser Ala Pro Ser Leu Phe Ser Thr Thr Tyr Ser Trp
            100                 105                 110

```
Thr Lys Met Ala Asn Ile Ile Phe Leu Asp Gln Pro Val Gly Ser Gly
        115                 120                 125

Phe Ser Tyr Ser Lys Thr Pro Ile Asp Lys Thr Gly Asp Ile Ser Glu
        130                 135                 140

Val Lys Arg Thr His Glu Phe Leu Gln Lys Trp Leu Ser Arg His Pro
145                 150                 155                 160

Gln Tyr Phe Ser Asn Pro Leu Tyr Val Val Gly Asp Ser Tyr Ser Gly
                165                 170                 175

Met Ile Val Pro Ala Leu Val Gln Glu Ile Ser Gln Gly Asn Tyr Ile
            180                 185                 190

Cys Cys Glu Pro Pro Ile Asn Leu Gln Gly Tyr Met Leu Gly Asn Pro
            195                 200                 205

Val Thr Tyr Met Asp Phe Glu Gln Asn Phe Arg Ile Pro Tyr Ala Tyr
        210                 215                 220

Gly Met Gly Leu Ile Ser Asp Glu Ile Tyr Glu Pro Met Lys Arg Ile
225                 230                 235                 240

Cys Asn Gly Asn Tyr Tyr Asn Val Asp Pro Ser Asn Thr Gln Cys Leu
                245                 250                 255

Lys Leu Thr Glu Glu Tyr His Lys Cys Thr Ala Lys Ile Asn Ile His
            260                 265                 270

His Ile Leu Thr Pro Asp Cys Asp Val Thr Asn Val Thr Ser Pro Asp
        275                 280                 285

Cys Tyr Tyr Tyr Pro Tyr His Leu Ile Glu Cys Trp Ala Asn Asp Glu
290                 295                 300

Ser Val Arg Glu Ala Leu His Ile Glu Lys Gly Ser Lys Gly Lys Trp
305                 310                 315                 320

Ala Arg Cys Asn Arg Thr Ile Pro Tyr Asn His Asp Ile Val Ser Ser
                325                 330                 335

Ile Pro Tyr His Met Asn Asn Ser Ile Ser Gly Tyr Arg Ser Leu Ile
            340                 345                 350

Tyr Ser Gly Asp His Asp Ile Ala Val Pro Phe Leu Ala Thr Gln Ala
        355                 360                 365

Trp Ile Arg Ser Leu Asn Tyr Ser Pro Ile His Asn Trp Arg Pro Trp
370                 375                 380

Met Ile Asn Asn Gln Ile Ala Gly Tyr Thr Arg Ala Tyr Ser Asn Lys
385                 390                 395                 400

Met Thr Phe Ala Thr Ile Lys Gly Gly Gly His Thr Ala Glu Tyr Arg
                405                 410                 415

Pro Asn Glu Thr Phe Ile Met Phe Gln Arg Trp Ile Ser Gly Gln Pro
            420                 425                 430

Leu

<210> SEQ ID NO 2
<211> LENGTH: 28
<212> TYPE: DNA
<213> ORGANISM: Artificial Sequence
<220> FEATURE:
<221> NAME/KEY: misc_feature
<223> OTHER INFORMATION: primer

<400> SEQUENCE: 2
tcatgacctc tatcgtcaag tttcttcc                              28

<210> SEQ ID NO 3
<211> LENGTH: 6
```

```
<212> TYPE: DNA
<213> ORGANISM: Artificial Sequence
<220> FEATURE:
<221> NAME/KEY: misc_feature
<223> OTHER INFORMATION: primer

<400> SEQUENCE: 3 tcatga                                                                  6

<210> SEQ ID NO 4
<211> LENGTH: 25
<212> TYPE: DNA
<213> ORGANISM: Artificial Sequence
<220> FEATURE:
<221> NAME/KEY: misc_feature
<223> OTHER INFORMATION: primer

<400> SEQUENCE: 4
gtcgacttac aggggttggc cactg                                            25

<210> SEQ ID NO 5
<211> LENGTH: 1302
<212> TYPE: DNA
<213> ORGANISM: Arabidopsis thaliana

<400> SEQUENCE: 5
atgagtttga aaataaagtt tctgcttctg cttgtcttgt atcatcatgt tgattctgcc      60
tctatcgtca agtttcttcc tggttttgaa ggccctcttc ctttcgaact tgaaaccggg     120
tacattggta ttggtgagga cgagaatgtg caatttttct actatttcat caaatctgaa     180
aacaatccaa agaagatcct cttcttata tggttaaatg gaggacctgg atgttcttgt     240
cttggtggta ttattttga gaacggaccg gtgggtttga gtttgaggt gttcaacgga     300
agtgctcctt ctttgttctc tactacatat tcatggacaa gatggcaaa cattatattc     360
ttggatcagc cagtaggatc tggcttctcc tactcaaaaa ctccaattga taaaactggt     420
gacataagtg aagtaaagag gacccatgag tttcttcaaa agtggctaag caggcatcca     480
caatatttct ccaaccctt atatgtagtt ggagattctt attccggtat gattgtcccg     540
gccctcgttc aagaaatctc acaaggaaat tatatatgtt gcgaacctcc tataaatcta     600
cagggttata tgcttggaaa ccctgtaaca tatatggact tgaacaaaa cttccgcatt     660
ccatatgctt atggtatggg attaatctcc gacgaaatct atgagccaat gaagagaatc     720
tgcaacggaa attattacaa tgtggatcca tctaacacac aatgtttgaa acttactgaa     780
gaatatcata agtgcactgc caaaataaat atccatcaca tattaacacc agattgcgat     840
gtaaccaatg taacatctcc tgattgttat tattatccat atcatctcat tgaatgttgg     900
gctaacgacg agagcgttcg cgaagctctt catattgaaa agggtagtaa aggaaaatgg     960
gcgcgatgta atcggactat tccatacaat cacgacattg taagcagcat accatatcac    1020
atgaataaca gcatcagtgg ataccgatct cttatttaca gtggtgatca cgacatcgcg    1080
gtccctttc ttgcaactca gcctggata agatctctca attactcccc cattcataac    1140
tggaggccat ggatgataaa caatcaaatc gctggataca cgagagctta ttccaataag    1200
atgacatttg ctactatcaa aggaggtgga cacacggcag agtatagacc aaacgagacc    1260
tttatcatgt tccaaaggtg gatcagtggc caaccctgt aa                        1302

<210> SEQ ID NO 6
<211> LENGTH: 1256
<212> TYPE: DNA
```

<210> SEQ ID NO 7
<211> LENGTH: 415
<212> TYPE: PRT
<213> ORGANISM: Arabidopsis thaliana

<400> SEQUENCE: 6

```
tcatgacctc tatcgtcaag tttcttcctg gttttgaagg ccctcttcct ttcgaacttg      60
aaaccgggta cattggtatt ggtgaggacg agaatgtgca attttctac tatttcatca     120
aatctgaaaa caatccaaaa gaagatcctc ttcttatatg gttaaatgga ggacctggat     180
gttcttgtct tggtggtatt attttgaga acggaccggt gggtttgaag tttgaggtgt     240
tcaacggaag tgctccttct ttgttctcta ctacatattc atggacaaag atggcaaaca    300
ttatattctt ggatcagcca gtaggatctg gcttctccta ctcaaaaact ccaattgata    360
aaactggtga cataagtgaa gtaaagagga cccatgagtt tcttcaaaag tggctaagca    420
ggcatccaca atatttctcc aacccttat atgtagttgg agattcttat tccggtatga    480
ttgtcccggc cctcgttcaa gaaatctcac aaggaaatta tatatgttgc gaacctccta    540
taaatctaca gggttatatg cttggaaacc ctgtaacata tatggacttt gaacaaaact    600
tccgcattcc atatgcttat ggtatgggat taatctccga cgaaatctat gagccaatga    660
agagaatctg caacggaaat tattacaatg tggatccatc taacacacaa tgtttgaaac    720
ttactgaaga atatcataag tgcactgcca aaataaatat ccatcacata ttaacaccag    780
attgcgatgt aaccaatgta acatctcctg attgttatta ttatccatat catctcattg    840
aatgttgggc taacgacgag agcgttcgcg aagctcttca tattgaaaag ggtagtaaag    900
gaaaatgggc gcgatgtaat cggactattc catacaatca cgacattgta agcagcatac    960
catatcacat gaataacagc atcagtggat accgatctct tatttacagt ggtgatcacg   1020
acatcgcggt cccttttctt gcaactcaag cctggataag atctctcaat tactccccca   1080
ttcataactg gaggccatgg atgataaaca atcaaatcgc tggatacacg agagcttatt   1140
ccaataagat gacatttgct actatcaaag gaggtggaca cacggcagag tatagaccaa   1200
acgagacctt tatcatgttc caaggtgga tcagtggcca acccctgtaa gtcgac       1256
```

<210> SEQ ID NO 7
<211> LENGTH: 415
<212> TYPE: PRT
<213> ORGANISM: Arabidopsis thaliana

<400> SEQUENCE: 7

```
Met Thr Ser Ile Val Lys Phe Leu Pro Gly Phe Glu Gly Pro Leu Pro
1               5                   10                  15
Phe Glu Leu Glu Thr Gly Tyr Ile Gly Ile Gly Glu Asp Glu Asn Val
            20                  25                  30
Gln Phe Phe Tyr Tyr Phe Ile Lys Ser Glu Asn Asn Pro Lys Glu Asp
        35                  40                  45
Pro Leu Leu Ile Trp Leu Asn Gly Gly Pro Gly Cys Ser Cys Leu Gly
    50                  55                  60
Gly Ile Ile Phe Glu Asn Gly Pro Val Gly Leu Lys Phe Glu Val Phe
65                  70                  75                  80
Asn Gly Ser Ala Pro Ser Leu Phe Ser Thr Thr Tyr Ser Trp Thr Lys
                85                  90                  95
Met Ala Asn Ile Ile Phe Leu Asp Gln Pro Val Gly Ser Gly Phe Ser
            100                 105                 110
Tyr Ser Lys Thr Pro Ile Asp Lys Thr Gly Asp Ile Ser Glu Val Lys
        115                 120                 125
Arg Thr His Glu Phe Leu Gln Lys Trp Leu Ser Arg His Pro Gln Tyr
```

```
                130                 135                 140
Phe Ser Asn Pro Leu Tyr Val Val Gly Asp Ser Tyr Ser Gly Met Ile
145                 150                 155                 160

Val Pro Ala Leu Val Gln Glu Ile Ser Gln Gly Asn Tyr Ile Cys Cys
                165                 170                 175

Glu Pro Pro Ile Asn Leu Gln Gly Tyr Met Leu Gly Asn Pro Val Thr
                180                 185                 190

Tyr Met Asp Phe Glu Gln Asn Phe Arg Ile Pro Tyr Ala Tyr Gly Met
                195                 200                 205

Gly Leu Ile Ser Asp Glu Ile Tyr Glu Pro Met Lys Arg Ile Cys Asn
                210                 215                 220

Gly Asn Tyr Tyr Asn Val Asp Pro Ser Asn Thr Gln Cys Leu Lys Leu
225                 230                 235                 240

Thr Glu Glu Tyr His Lys Cys Thr Ala Lys Ile Asn Ile His His Ile
                245                 250                 255

Leu Thr Pro Asp Cys Asp Val Thr Asn Val Thr Ser Pro Asp Cys Tyr
                260                 265                 270

Tyr Tyr Pro Tyr His Leu Ile Glu Cys Trp Ala Asn Asp Glu Ser Val
                275                 280                 285

Arg Glu Ala Leu His Ile Glu Lys Gly Ser Lys Gly Lys Trp Ala Arg
290                 295                 300

Cys Asn Arg Thr Ile Pro Tyr Asn His Asp Ile Val Ser Ser Ile Pro
305                 310                 315                 320

Tyr His Met Asn Asn Ser Ile Ser Gly Tyr Arg Ser Leu Ile Tyr Ser
                325                 330                 335

Gly Asp His Asp Ile Ala Val Pro Phe Leu Ala Thr Gln Ala Trp Ile
                340                 345                 350

Arg Ser Leu Asn Tyr Ser Pro Ile His Asn Trp Arg Pro Trp Met Ile
                355                 360                 365

Asn Asn Gln Ile Ala Gly Tyr Thr Arg Ala Tyr Ser Asn Lys Met Thr
                370                 375                 380

Phe Ala Thr Ile Lys Gly Gly Gly His Thr Ala Glu Tyr Arg Pro Asn
385                 390                 395                 400

Glu Thr Phe Ile Met Phe Gln Arg Trp Ile Ser Gly Gln Pro Leu
                405                 410                 415
```

<210> SEQ ID NO 8
<211> LENGTH: 27
<212> TYPE: DNA
<213> ORGANISM: Artificial Sequence
<220> FEATURE:
<221> NAME/KEY: misc_feature
<223> OTHER INFORMATION: primer

<400> SEQUENCE: 8
gagaatatca tgagtttgaa aataaag                                27

<210> SEQ ID NO 9
<211> LENGTH: 1317
<212> TYPE: DNA
<213> ORGANISM: Arabidopsis thaliana

<400> SEQUENCE: 9
gagaatatca tgagtttgaa aataaagttt ctgcttctgc ttgtcttgta tcatcatgtt    60
gattctgcct ctatcgtcaa gtttcttcct ggttttgaag ccctcttcc tttcgaactt    120 gaaaccgggt acattggtat tggtgaggac gagaatgtgc aattttttcta ctatttcatc    180

```
aaatctgaaa caatccaaa agaagatcct cttcttatat ggttaaatgg aggacctgga    240
tgttcttgtc ttggtggtat tattttgag aacggaccgg tgggtttgaa gtttgaggtg    300
ttcaacggaa gtgctccttc tttgttctct actacatatt catggacaaa gatggcaaac    360
attatattct tggatcagcc agtaggatct ggcttctcct actcaaaaac tccaattgat    420
aaaactggtg acataagtga agtaaagagg acccatgagt ttcttcaaaa gtggctaagc    480
aggcatccac aatatttctc caaccctta tatgtagttg gagattctta ttccggtatg    540
attgtcccgg ccctcgttca agaaatctca caaggaaatt atatatgttg cgaacctcct    600
ataaatctac agggttatat gcttggaaac cctgtaacat atatggactt gaacaaaac    660 ttccgcattc catatgctta tggtatggga ttaatctccg acgaaatcta tgagccaatg    720
aagagaatct gcaacggaaa ttattacaat gtggatccat ctaacacaca atgtttgaaa    780
cttactgaag aatatcataa gtgcactgcc aaaataaata tccatcacat attaacacca    840
gattgcgatg taaccaatgt aacatctcct gattgttatt attatccata tcatctcatt    900
gaatgttggg ctaacgacga gagcgttcgc gaagctcttc atattgaaaa gggtagtaaa    960
ggaaaatggg cgcgatgtaa tcggactatt ccatacaatc acgacattgt aagcagcata   1020
ccatatcaca tgaataacag catcagtgga taccgatctc ttatttacag tggtgatcac   1080
gacatcgcgg tcccttttct tgcaactcaa gcctggataa gatctctcaa ttactccccc   1140
attcataact ggaggccatg gatgataaac aatcaaatcg ctggatacac gagagcttat   1200
tccaataaga tgacatttgc tactatcaaa ggaggtggac acacggcaga gtatagacca   1260
aacgagacct ttatcatgtt ccaaaggtgg atcagtggcc aacccctgta agtcgac     1317
```

<210> SEQ ID NO 10
<211> LENGTH: 32
<212> TYPE: DNA
<213> ORGANISM: Artificial Sequence
<220> FEATURE:
<221> NAME/KEY: misc_feature
<223> OTHER INFORMATION: primer

<400> SEQUENCE: 10

```
ctactcattt catatgtcac accccgcgtt aa                                    32
```

<210> SEQ ID NO 11
<211> LENGTH: 34
<212> TYPE: DNA
<213> ORGANISM: Artificial Sequence
<220> FEATURE:
<221> NAME/KEY: misc_feature
<223> OTHER INFORMATION: primer

<400> SEQUENCE: 11

```
catcttacta gatctttagt acaacggtga cgcc                                  34
```

<210> SEQ ID NO 12
<211> LENGTH: 495
<212> TYPE: DNA
<213> ORGANISM: Escherichia coli

<400> SEQUENCE: 12

```
atgtcacacc ccgcgttaac gcaactgcgt gcgctgcgct attgtaaaga gatccctgcc     60
ctggatccgc aactgctcga ctggctgttg ctggaggatt ccatgacaaa acgttttgaa    120
cagcagggaa aacggtaag cgtgacgatg atccgcgaag ggtttgtcga gcagaatgaa    180
```

```
atccccgaag aactgccgct gctgccgaaa gagtctcgtt actggttacg tgaaattttg      240
ttatgtgccg atggtgaacc gtggcttgcc ggtcgtaccg tcgttcctgt gtcaacgtta      300
agcgggccgg agctggcgtt acaaaaattg ggtaaaacgc cgttaggacg ctatctgttc      360
acatcatcga cattaacccg ggactttatt gagataggcc gtgatgccgg gctgtggggg      420
cgacgttccc gcctgcgatt aagcggtaaa ccgctgttgc taacagaact gttttttaccg     480 gcgtcaccgt tgtac                                                        495
```

```
<210> SEQ ID NO 13
<211> LENGTH: 165
<212> TYPE: PRT
<213> ORGANISM: Escherichia coli

<400> SEQUENCE: 13
```

```
Met Ser His Pro Ala Leu Thr Gln Leu Arg Ala Leu Arg Tyr Cys Lys
1               5                   10                  15

Glu Ile Pro Ala Leu Asp Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Gln Asn Glu Ile Pro Glu Glu
    50                  55                  60

Leu Pro Leu Pro Lys Glu Ser Arg Tyr Trp Leu Arg Glu Ile Leu
65                  70                  75                  80

Leu Cys Ala Asp Gly Glu Pro Trp Leu Ala Gly Arg Thr Val Val Pro
                85                  90                  95

Val Ser Thr Leu Ser Gly Pro Glu Leu Ala Leu Gln Lys Leu Gly Lys
            100                 105                 110

Thr Pro Leu Gly Arg Tyr Leu Phe Thr Ser Ser Thr Leu Thr Arg Asp
        115                 120                 125

Phe Ile Glu Ile Gly Arg Asp Ala Gly Leu Trp Gly Arg Arg Ser Arg
    130                 135                 140

Leu Arg Leu Ser Gly Lys Pro Leu Leu Leu Thr Glu Leu Phe Leu Pro
145                 150                 155                 160

Ala Ser Pro Leu Tyr
            165
```

```
<210> SEQ ID NO 14
<211> LENGTH: 39
<212> TYPE: DNA
<213> ORGANISM: Artificial Sequence
<220> FEATURE:
<221> NAME/KEY: misc_feature
<223> OTHER INFORMATION: primer

<400> SEQUENCE: 14
ctactcactt agatctccat ggcttcctct gtcatttct                              39
```

```
<210> SEQ ID NO 15
<211> LENGTH: 32
<212> TYPE: DNA
<213> ORGANISM: Artificial Sequence
<220> FEATURE:
<221> NAME/KEY: misc_feature
<223> OTHER INFORMATION: primer

<400> SEQUENCE: 15
catcttactc atatgccaca cctgcatgca gc                                     32
```

<210> SEQ ID NO 16
<211> LENGTH: 684
<212> TYPE: DNA
<213> ORGANISM: Artificial Sequence
<220> FEATURE:
<221> NAME/KEY: misc_feature
<223> OTHER INFORMATION: open reading frame of the chloroplast-targeted
    CPL fusion protein

<400> SEQUENCE: 16

```
atggcttcct ctgtcatttc ttcagcagct gttgccacac gcagcaatgt tacacaagct      60
agcatggttg cacctttcac tggtctcaaa tcttcagcca ctttccctgt tacaaagaag     120
caaaaccttg acatcacttc cattgctagc aatggtggaa gagttagctg catgcaggtg     180
tggcatatgt cacaccccgc gttaacgcaa ctgcgtgcgc tgcgctattg taaagagatc     240
cctgccctgg atccgcaact gctcgactgg ctgttgctgg aggattccat gacaaaacgt     300
tttgaacagc agggaaaaac ggtaagcgtg acgatgatcc gcgaagggtt tgtcgagcag     360
aatgaaatcc ccgaagaact gccgctgctg ccgaaagagt ctcgttactg gttacgtgaa     420
attttgttat gtgccgatgg tgaaccgtgg cttgccggtc gtaccgtcgt tcctgtgtca     480
acgttaagcg gccggagct ggcgttacaa aaattgggta aaacgccgtt aggacgctat      540
ctgttcacat catcgacatt aacccgggac tttattgaga taggccgtga tgccgggctg     600
tgggggcgac gttccgcct gcgattaagc ggtaaaccgc tgttgctaac agaactgttt     660
ttaccggcgt caccgttgta ctaa                                             684
```

<210> SEQ ID NO 17
<211> LENGTH: 227
<212> TYPE: PRT
<213> ORGANISM: Artificial Sequence
<220> FEATURE:
<221> NAME/KEY: VARIANT
<222> LOCATION: (1)..(227)
<223> OTHER INFORMATION: open reading frame of the chloroplast-targeted
    CPL fusion protein

<400> SEQUENCE: 17

```
Met Ala Ser Ser Val Ile Ser Ser Ala Ala Val Ala Thr Arg Ser Asn
1               5                   10                  15

Val Thr Gln Ala Ser Met Val Ala Pro Phe Thr Gly Leu Lys Ser Ser
            20                  25                  30

Ala Thr Phe Pro Val Thr Lys Lys Gln Asn Leu Asp Ile Thr Ser Ile
        35                  40                  45

Ala Ser Asn Gly Gly Arg Val Ser Cys Met Gln Val Trp His Met Ser
    50                  55                  60

His Pro Ala Leu Thr Gln Leu Arg Ala Leu Arg Tyr Cys Lys Glu Ile
65                  70                  75                  80

Pro Ala Leu Asp Pro Gln Leu Leu Asp Trp Leu Leu Leu Glu Asp Ser
                85                  90                  95

Met Thr Lys Arg Phe Glu Gln Gln Gly Lys Thr Val Ser Val Thr Met
            100                 105                 110

Ile Arg Glu Gly Phe Val Glu Gln Asn Glu Ile Pro Glu Glu Leu Pro
        115                 120                 125

Leu Leu Pro Lys Glu Ser Arg Tyr Trp Leu Arg Glu Ile Leu Leu Cys
    130                 135                 140

Ala Asp Gly Glu Pro Trp Leu Ala Gly Arg Thr Val Val Pro Val Ser
145                 150                 155                 160
```

-continued

```
Thr Leu Ser Gly Pro Glu Leu Ala Leu Gln Lys Leu Gly Lys Thr Pro
                165                 170                 175

Leu Gly Arg Tyr Leu Phe Thr Ser Ser Thr Leu Thr Arg Asp Phe Ile
            180                 185                 190

Glu Ile Gly Arg Asp Ala Gly Leu Trp Gly Arg Arg Ser Arg Leu Arg
        195                 200                 205

Leu Ser Gly Lys Pro Leu Leu Leu Thr Glu Leu Phe Leu Pro Ala Ser
    210                 215                 220

Pro Leu Tyr
225

<210> SEQ ID NO 18
<211> LENGTH: 34
<212> TYPE: DNA
<213> ORGANISM: Artificial Sequence
<220> FEATURE:
<221> NAME/KEY: misc_feature
<223> OTHER INFORMATION: primer

<400> SEQUENCE: 18
ctactcattt gaagactgca tgcaggtgtg gcat                            34

<210> SEQ ID NO 19
<211> LENGTH: 34
<212> TYPE: DNA
<213> ORGANISM: Artificial Sequence
<220> FEATURE:
<221> NAME/KEY: misc_feature
<223> OTHER INFORMATION: primer

<400> SEQUENCE: 19
catcttactg tcgactttag tacaacggtg acgc                            34
```